United States Patent
Huang et al.

(10) Patent No.: US 9,714,315 B2
(45) Date of Patent: Jul. 25, 2017

(54) MOISTURE CURABLE SILYLATED POLYMER COMPOSITIONS CONTAINING REACTIVE MODIFIERS

(71) Applicant: Momentive Performance Materials Inc., Waterford, NY (US)

(72) Inventors: Misty Huang, New City, NY (US); Richard W. Cruse, Yorktown Heights, NY (US); Benjamin Falk, Yorktown Heights, NY (US); Eric Pohl, Mount Kisco, NY (US); Shiu-Chin Su, Croton-on-Hudson, NY (US); Jeries Nesheiwat, Yonkers, NY (US); Philbert Ramdatt, New York, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/327,059

(22) Filed: Jul. 9, 2014

(65) Prior Publication Data
US 2014/0323650 A1    Oct. 30, 2014

Related U.S. Application Data

(63) Continuation of application No. 12/767,715, filed on Apr. 26, 2010, now Pat. No. 8,809,479.

(60) Provisional application No. 61/174,768, filed on May 1, 2009.

(51) Int. Cl.
| | | |
|---|---|---|
| C08L 83/00 | (2006.01) | |
| C08G 18/83 | (2006.01) | |
| C08G 18/10 | (2006.01) | |
| C08G 18/28 | (2006.01) | |
| C09J 175/04 | (2006.01) | |
| C09J 201/10 | (2006.01) | |
| C07F 7/18 | (2006.01) | |
| C08G 18/48 | (2006.01) | |
| C09D 175/08 | (2006.01) | |
| C09J 175/08 | (2006.01) | |

(52) U.S. Cl.
CPC ............. *C08G 18/837* (2013.01); *C07F 7/18* (2013.01); *C08G 18/10* (2013.01); *C08G 18/289* (2013.01); *C08G 18/48* (2013.01); *C09D 175/08* (2013.01); *C09J 175/04* (2013.01); *C09J 175/08* (2013.01); *C09J 201/10* (2013.01)

(58) Field of Classification Search
CPC ........... C07F 7/18; C08G 18/48; C08L 101/10
See application file for complete search history.

(56) References Cited

U.S. PATENT DOCUMENTS

| | | | |
|---|---|---|---|
| 3,101,277 A | 8/1963 | Eder et ai. | |
| 3,627,722 A | 12/1971 | Seiter | |
| 5,214,119 A | 5/1993 | Leihr et al. | |
| 5,719,251 A * | 2/1998 | Wilczek ................... | C07F 7/12 427/387 |
| 5,990,257 A | 11/1999 | Johnston et al. | |
| 6,001,946 A | 12/1999 | Waldman et al. | |
| 6,197,912 B1 | 3/2001 | Huang et al. | |
| 6,204,350 B1 * | 3/2001 | Liu et al. ......................... | 528/23 |
| 6,355,317 B1 | 3/2002 | Reid et al. | |
| 6,486,289 B1 | 11/2002 | Yamaguchi et al. | |
| 6,498,210 B1 | 12/2002 | Wang et al. | |
| 7,319,128 B2 | 1/2008 | Ziche et al. | |
| 7,867,619 B2 | 1/2011 | Jucker et al. | |
| 8,809,479 B2 * | 8/2014 | Huang et al. .................. | 528/30 |
| 2006/0079645 A1 | 4/2006 | Hasegawa et al. | |
| 2006/0173121 A1 | 8/2006 | Tamai | |
| 2006/0189736 A1 | 8/2006 | Mori et al. | |
| 2010/0317796 A1 | 12/2010 | Huang et al. | |
| 2013/0245194 A1 | 9/2013 | Huang et al. | |

FOREIGN PATENT DOCUMENTS

| | | |
|---|---|---|
| EP | 0931800 | 7/1999 |
| EP | 1035170 | 9/2000 |
| EP | 1462500 | 9/2004 |
| JP | 2009/508989 A | 3/2009 |
| WO | 2007/035255 A1 | 3/2007 |
| WO | 2008/156611 A1 | 12/2008 |

OTHER PUBLICATIONS

International Search Report mailed Aug. 4, 2010.

* cited by examiner

*Primary Examiner* — Kuo-Liang Peng
(74) *Attorney, Agent, or Firm* — James C. Abruzzo

(57) ABSTRACT

A moisture-curable resin composition comprising (a) a moisture-curable polymer having at least one hydrolysable silyl group; (b) a reactive modifier; (c) a catalyst for catalyzing the reaction between the moisture-curable polymer (a) and reactive modifier (b) under curing conditions; and optionally, the composition can contain one or more conventional components, including pigments, fillers, curing catalysts, dyes, plasticizers, thickeners, coupling agents, extenders, volatile organic solvents, wetting agents, tackifiers, crosslinking agents, thermoplastic polymers, ultraviolet stabilizers, and combination thereof. The moisture-curable resin composition is useful in the production of adhesives including hot melt adhesives, primers, sealants and coatings.

17 Claims, No Drawings

MOISTURE CURABLE SILYLATED POLYMER COMPOSITIONS CONTAINING REACTIVE MODIFIERS

This application claims priority as a continuation from U.S. patent application Ser. No. 12/767,715 filed Apr. 26, 2010, which claims priority of provisional application 61/174,768 dated May 1, 2009, the entire contents both of which are incorporated herein by reference in their entirety.

FIELD OF THE INVENTION

The present invention relates to moisture-curable resin compositions having low volatile organic content, yet possessing desired low viscosity, which upon curing provides a cured product having a desirable combination of high modulus and tensile strength. More particularly, the present invention relates to moisture-curable resin compositions containing silylated polymers and reactive modifiers and to moisture-curable sealant, adhesive including hot-melt adhesive, primer, and coating compositions containing these moisture-curable resin compositions.

BACKGROUND OF THE INVENTION

Hydrolysable silane-terminated polymers are commonly used in the marketplace of adhesives, sealants and coatings. This is at least partially attributed to their environmentally friendly, low volatile organic content characteristics. Certain hydrolysable silane-terminated polymers and their use in sealants, adhesives and coatings have been disclosed in the art. Illustratively, U.S. Pat. No. 3,627,722 discloses polyurethane sealants made from an isocyanate-terminated polymer, wherein at least five percent of the isocyanate groups are end-blocked with trialkoxysilyl groups. U.S. Pat. No. 7,319,128 discloses organyloxysilyl-terminated polymers obtained by reacting hydroxyl-terminated organic polymers with isocyanato-functional silanes in the presence of a catalyst. U.S. Pat. No. 6,001,946 discloses curable silane-terminated polymers based upon maleate-adducts of amino-alkylsilanes.

Unfortunately, as compared with conventional urethane-based adhesives and sealants, cured products made from hydrolysable silane-terminated polymers tend to have lower modulus and tensile strength than might be desired. Efforts have been made to improve the modulus and tensile strength of the products made from the silylated polymers. Illustratively, U.S. Pat. No. 5,990,257 discloses silylated polyurethanes prepared by using extremely low-unsaturation polyether polyols in the formation of the polyurethane prepolymers that are silylated. The '257 patent discloses that these silylated polyurethanes exhibit improved mechanical properties upon curing to a low-tack sealant. Likewise, U.S. Pat. No. 6,498,210 describes a silylated polyurethane polymer containing unreacted isocyanate groups or low molecular weight terminators. The '210 patent discloses that such polymers provide improved tensile strength after cure. Moreover, U.S. Pat. No. 6,001,946 discloses a class of N-silylalkyl-aspartic acid ester-terminated polyurethane polymers and sealant formulations made from the silylated polymers that are said to exhibit improved elongation, tensile strength and tear resistance.

Heretofore, resin compositions employing hydrolysable silane-terminated polymers typically required the use of volatile organic solvents in order to provide a desirable viscosity prior to curing. In order to meet the increasing stringent environmental regulations, efforts have been previously made to reduce the volatile organic content of the resin compositions. For example, U.S. Pat. No. 5,719,251 discloses certain reactive organosilicon compounds that can be used to provide coatings, adhesives, and the like that allegedly have low volatile organic content. However, this patent does not disclose any compositions exhibiting a combination of low volatile organic content and low viscosity before curing and improved modulus and tensile strength after cure.

In the field of hot melt applications, thermoplastic polymers containing tackifiers, fillers and other additives are typically utilized. These hot melt compositions are solid at room temperature but flow at elevated temperatures. Because the compositions are made up primarily of an uncrosslinked thermoplastic component, they are often of low modulus and are susceptible to creep and cold flow under static loads making them unsuitable for many applications where strength of the adhesive joint is critical such as that required for bonding together heavy metal sheets in the construction of truck trailers. The weight on the joints, combined with vibration and environmental heat and moisture resulting from exposure to sun in hot and humid climates, can cause adhesive joints made with known hot melt adhesives to distort and eventually fail.

Moisture-curable hot melt adhesive compositions are known in the art which partially address the foregoing deficiencies. These compositions often contain a thermoplastic component such as a chlorinated paraffin or plasticizer, styrene block copolymer, butyl rubber or poly-α-olefin, and a silylated polyurethane based upon polyols or polyamines containing polybutadiene, polyester, acrylic, polycarbonate or polythioether backbones. Moisture-curable hot melt adhesive compositions contain a continuous phase of the thermoplastic component in which the silylated urethane is dispersed and crosslinked during the application process. The thermoplastic continuous phase, however, remains susceptible to creep and cold flow when placed under static loads. Where the silylated polyurethane component of a moisture-curable holt melt resin composition is incompatible with its thermoplastic component, little if any crosslinking will occur between the two thus giving rise to phase separation of the cured material. Single component and moisture-curable hot melt compositions may therefore exhibit insufficient strength and modulus due to the thermoplastic polymer debonding from the silylated polyurethane under static loads. The silylated polyurethane phase may also be too elastomeric and too low in modulus to provide the desired levels of bond strength.

Accordingly, there is a continuing need in the hydrolysable silane-terminated polymers community for a resin composition that has low volatile organic content and possesses desirably low viscosity prior to cure and, which upon cure, exhibits high modulus and tensile strength. The present invention provides one solution to that need.

SUMMARY OF THE INVENTION

One aspect of the present invention relates to a moisture-curable resin composition comprising (a) a moisture-curable polymer having at least one hydrolysable silyl group; (b) a reactive modifier; and (c) a catalyst for catalyzing the reaction between the moisture-curable polymer (a) and reactive modifier (b) under curing conditions. Optionally, the composition can contain one or more conventional components, including fillers, plasticizers, thixothropes, ultraviolet stabilizers, hydroxyl-terminated polymers and adhesion promoters.

The reactive modifier (b) of the present invention is a compound of the general Formula (1) or (2):

(Formula 1); and

(Formula 2)

wherein:

$G^1$ is selected from the group consisting of a divalent or polyvalent cyclic hydrocarbon group containing from 5 to 16 carbon atoms, a divalent or polyvalent cyclic heterocarbon group containing from 3 to 16 carbon atoms wherein the heteroatoms are selected from the group consisting of oxygen, silicon and sulfur; and a divalent or polyvalent cyclic silicone group containing from 3 to 8 silicon atoms and from 3 to 8 oxygen atoms;

$G^2$ is selected from the group consisting of a monovalent or divalent linear hydrocarbon group containing from 3 to 16 carbon atoms; and a monovalent or divalent linear heterocarbon containing from 3 to 16 carbon atoms wherein the heteroatoms are selected from the group consisting of oxygen, silicon and sulfur;

each occurrence of $R^1$ is independently selected from the group consisting of a covalent bond between the silicon atom and $G^1$, a divalent hydrocarbon group containing from 1 to 18 carbon atoms, and optionally the divalent hydrocarbon group contains at least one heteroatom selected from the group consisting of oxygen, silicon and sulfur;

each occurrence of $R^2$ is monovalent hydrocarbon containing from 1 to 12 carbon atoms;

each occurrence of $R^3$ is monovalent hydrocarbon containing from 1 to 12 carbon atoms;

each occurrence of $R^4$ is monovalent hydrocarbon containing from 1 to 12 carbon atoms;

each occurrence of $R^5$ is monovalent hydrocarbon containing from 1 to 12 carbon atoms;

each occurrence of a, b, c and d is independently an integer, wherein a is 0 to 2; b is 2 to 6; c is 0 to 2; and d is 1 or 2 with the provisos that (i) when $R^1$ is a chemical bond, then the silicon atom is covalently bonded to a carbon atom of $G^1$;

(ii) when $R^1$ contains a heteroatom, the silicon atom is bonded to a carbon atom of $R^1$;

(iii) when $G^2$ contains a heteroatom, the terminal atoms of $G^2$ are carbon atoms; and (iv) when the silicon atom is attached to $G^2$, the silicon atom is covalently bonded to a terminal carbon of $G^2$.

In another aspect, the present invention is directed to a cured composition prepared from curing the aforementioned moisture-curable composition.

In yet another aspect, the present invention relates to sealants including hot melt sealants, adhesives, including hot-melt adhesives, primers and coatings containing the aforementioned moisture-curable composition.

These and other aspects will become apparent upon reading the following detailed description of the invention.

DETAILED DESCRIPTION OF THE INVENTION

The present invention relates to moisture-curable resin compositions comprising: (a) moisture-curable polymer having at least one hydrolysable silyl group; (b) reactive modifier of the general Formula 1 or 2; and (c) a catalyst for catalyzing the reaction between the moisture-curable polymer (a) and reactive modifier (b) under curing conditions. The moisture-curable resin composition according to the present invention has a low volatile organic content, yet at the same time has a low viscosity. The resin composition is stable under moisture free conditions. Upon application and in the presence of moisture, the moisture-curable polymer (a) and reactive modifier (b) hydrolyzes and reacts with themselves and with each other to provide a cured elastomer having high modulus.

The moisture-curable polymer (a) has at least one hydrolysable silyl group that is bonded to the polymer chain through an ether (—O—) linking group or carbonyl group, in which the carbonyl is bonded to heteroatoms selected from the group consisting of oxygen, nitrogen and sulfur, with the proviso that at least one heteroatom is nitrogen.

In one embodiment of the present invention the moisture-curable polymer (a) has the general Formula (3):

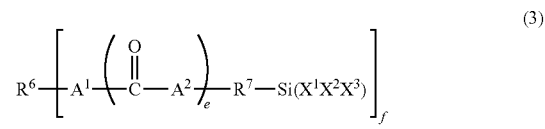
(3)

wherein:

each occurrence of $R^6$ is independently a monovalent or polyvalent organic polymer fragment having a number average molecular weight of from 500 to 25,000 grams per mole (g/mol);

each occurrence of $R^7$ is independently a divalent hydrocarbylene group containing from 1 to 12 carbon atoms which is selected from the group consisting of divalent alkylene, alkenylene, arenylene, arylene and aralkylene, and, optionally, the divalent hydrocarbylene group contains at least one heteroatom selected from the group consisting of oxygen, nitrogen and sulfur;

each occurrence of $A^1$ is independently selected from divalent oxygen (—O—), sulfur (—S—) or substituted nitrogen of the structure $(-)_2NR^8$, wherein $R^8$ is hydrogen, alkyl, alkenyl, arenyl, aryl, aralkyl or —$R^7SiX^1X^2X^3$ group, wherein each $R^8$, other than hydrogen, contains from 1 to 18 carbon atoms, and with the provisos that when $A^1$ is oxygen or sulfur, then $A^2$ is $(-)_2NR^8$ and when e is 0, then $A^1$ is oxygen;

each occurrence of $A^2$ is independently selected from divalent oxygen (—O—), sulfur (—S—) or substituted nitrogen of the structure $(-)_2NR^8$, —$NR^8(C=O)NR^8$—, —$NR^8(C=O)O$—, and —$NR^8(C=O)S$—, wherein $R^8$ is hydrogen, alkyl, alkenyl, arenyl, aryl, aralkyl or —$R^7SiX^1X^2X^3$ group, wherein each $R^8$, other than hydrogen, contains from 1 to 18 carbon atoms, and with the proviso that when $A^2$ is oxygen or sulfur, then $A^1$ is $(-)_2NR^8$;

each occurrence of $X^1$ is independently $R^9O$—, wherein each $R^9$ is independently selected from the group consisting of hydrogen, alkyl, alkenyl, arenyl, aryl, and aralkyl groups, wherein each $R^9$, other than hydrogen, contains from 1 to 18 carbon atoms and, optionally, contains at least one oxygen or sulfur atom;

each occurrence of $X^2$ and $X^3$ is independently selected from the group consisting of $R^9O$— and $R^{10}$ wherein each $R^9$ is independently selected from the group consisting of hydrogen, alkyl, alkenyl, arenyl, aryl, and aralkyl, wherein each $R^9$, other than hydrogen, contains from 1 to 18 carbon atoms and, optionally, contains at least one oxygen or sulfur atom and each $R^{10}$ is independently an alkyl group containing from 1 to 6 carbon atoms; and, each occurrence of subscripts e and f is independently an integer wherein e is 0 or 1 and f is 1 to 6.

As used herein, "alkyl" includes straight, branched and cyclic alkyl groups; "alkenyl" includes any straight, branched, or cyclic alkenyl group containing one or more carbon-carbon double bonds, where the point of substitution can be either at a carbon-carbon double bond or elsewhere in the group; "aryl" includes any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents.

Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of aryls include, but are not limited to, phenyl and naphthalenyl. Specific examples of aralkyls include, but are not limited to, benzyl and phenethyl. Specific examples of arenyls include, but are not limited to, tolyl and xylyl.

The moisture-curable polymer (a), which include, but not limited to (1) isocyanatosilane-terminated polyurethane polymers as described in U.S. Pat. No. 5,990,257 and U.S. Pat. No. 7,319,128, which are incorporated herein by reference in their entireties; (2) aminosilane-terminated polyurethane prepolymers as described in U.S. Pat. No. 6,197,912 and U.S. Pat. No. 6,001,946, which are incorporated herein by reference in their entireties; and (3) the hydrolysable silane-terminated polyethers as described in U.S. Patent Application No. 2006/0173121, which is incorporated herein by reference in its entirety The moisture-curable polymer (a) may be present in the composition in an amount of from 30 weight percent to 95 weight percent based on the total weight of components (a), (b) and (c), preferably in an amount of from 50 weight percent to 90 weight percent based on the total weight of components (a), (b) and (c), and most preferably in an amount of from 60 weight percent to 80 weight percent based on the total weight of components (a), (b) and (c).

The moisture-curable polymer (a) can be prepared from a polyol reactant or a combination of polyol reactants. Combinations or mixtures of polyol reactants are often used to achieve specific physical properties of the moisture-cured polymer resin, such as flowability, tensile, modulus and adhesion. The number average molecular weight of the polyol reactant is specifically from 300 to 24,000 grams per mole (g/mol), and more specifically from 1,000 to 20,000 grams per mole. These polyols optionally contain other organic functional groups, including the non-limiting examples of urethane, thiourethane, urea, biuret, ester, thioester, ether, thioether, amide, and the like.

A moisture-curable polymer containing one silyl group can be used in combination with a moisture-curable polymer containing two or more silyl groups to lower the Tg and increase the flexibility of the moisture-curable polymer (a). The moisture-curable polymer containing one silyl group functions as a reactive plasticizer that becomes incorporated into the polymer network during cure. However, if the average hydroxyl-functionality polyol mixture is too low, then the moisture-curable silylated polymer resin composition may cure poorly. It is, therefore, preferable to have sufficient average functionality in the reactant polyols, such that the moisture-curable polymer (a) prepared from them cures on exposure to moisture. The average hydroxyl-functionality of the polyol reactant mixture is specifically from 1.6 to 6.0 hydroxyl group per polyol molecule, more specifically from 1.8 to 3.0 hydroxyl group per polyol molecule and most specifically, from 1.95 to 2.5 hydroxyl groups per polyol molecule.

The moisture-curable polymer (a) can be prepared from a blend of a low number average molecular weight polyol reactant and a high number average molecular weight polyol reactant. The moisture-curable polymer (a) prepared from this blend of polyol reactants after cure and at low strains has a high modulus, while maintaining high values for elongations at break. The number average molecular weight of the low molecular weight polyol is specifically from 300 to 2,000 grams per mole, more specifically from 500 to 1,200 grams per mole and most specifically from 800 to 1,000 grams per mole. The number average molecular weight of the high molecular weight polyol is specifically from 2,000 to 24,000 grams per mole, more specifically from 4,000 to 12,000 grams per mole and most specifically from 8,000 to 10,000 grams per mole. The weight ratio of low molecular weight polyol reactant to high molecular weight polyol reactant is specifically from 0.01 to 3, more specifically from 0.05 to 1 and most specifically from 0.2 to 0.5.

Representative non-limiting examples of polyols include hydroxyl-terminated polyalkylene oxides, such as hydroxyl-terminated polypropylene oxide, hydroxyl-terminated polyethylene oxide, and hydroxyl-terminated polybutylene oxide; polyoxyalkylene triols; polycaprolactone diols and triols; hydroxyl terminated unsaturated rubbers, such as hydroxyl-terminated polybutane diene copolymer; polyester diols and polyol made from saturated aliphatic diacids and diols or triols, unsaturated diacids and diols or triols, saturated polyacids and diols or aromatic diacids and diols or triols and the like; polytetramethylene glycols; and other diols or triols.

The polyols employed may have a very low unsaturation level and therefore high functionality. Said polyols are typically prepared using metal complex catalysts for the polymerization of alkylene oxide resulting in polyols having a low level of terminal ethylenic unsaturation. The polyols have a terminal ethylenic unsaturation that is specifically less than 0.4 milliequivalents per gram (meq/g) of polyol, more specifically less than 0.1 milliequivalents per gram of polyol and even more specifically, less than 0.02 milliequivalents per gram of polyol. The number average molecular weight of the polyols is specifically in the range between from 500 and 24.000 grams per mole and more specifically from 2000 to 12,000 grams per mole.

The moisture-curable polymer (a) may additionally include a hydroxyl-terminated polymer. The addition of hydroxyl-terminated polymer can further facilitate the condensation cure of the composition. In addition, the properties of the cured products are further enhanced on modulus, tensile strength as well as hardness, while the flexibility remains essentially the same or is slightly reduced in some cases.

The moisture-curable polymer (a) of the present invention can be prepared by any of several synthetic methods including those hereinafter described.

Synthetic Method 1: Reaction of a Polyol with a Polyisocyanate and then with a Hydrolysable Silane Containing Active Hydrogen-Functional Group to Provide a Moisture-Curable Polymer Containing at Least One Hydrolysable Silyl Group The above-mentioned hydroxyl-functional polyols are converted into isocyanate-terminated prepolymers in known manner by reaction with polyisocyanates. These prepolymers are prepared by reacting an excess of polyisocyanate with a polyol or a combination of polyols usually in the presence of a catalyst.

The isocyanate-terminated prepolymer after the reaction of the polyol with the polyisocyanate has the general Formula (4):

$$R^6(-N=C=O)_f \quad (4)$$

wherein $R^6$ and f have the aforestated meanings. It is understood that $R^6$ polymer fragment contains a urethane group as a result of the reaction of the polyol with an isocyanate group. According to one embodiment of the invention, isocyanate-terminated prepolymer is prepared by reacting diisocyanates with polyols at different ratios of NCO to OH that range specifically from 1.1 to 2.0, more specifically from 1.4 to 1.9 and most specifically from 1.5 to 1.8.

Suitable polyisocyanates include any from which polyurethane polymers can be prepared by the customary sequence of reaction with polyol to form a prepolymer. Useful diisocyanates include, for example, 2,4-toluene diisocyanate, 2,6-toluene diisocyanate, a mixture of 2,4- and 2,6-toluene diisocyanate isomers [most of the TDI from markets are the mixture], 4,4' diphenyl-methanediisocyanate, isophorone diisocyanate, dicyclohexylmethane-4,4'-diisocyanate, various liquid diphenylmethane-diisocyanates containing a mixture of 2,4- and 4,4' isomers, and the like, and mixtures thereof. Preferably, the isocyanate functional monomer employed is an isophorone diisocyanate (IPDI) available from Bayer under the trade name Desmodur I D 230 or tetramethylxylylene diisocyanate (TMXDI).

A catalyst may be used in the preparation of the above-mentioned isocyanate-terminated prepolymers. Suitable catalysts are metal salts or bases, and include the non-limiting examples of bismuth salts, such as bismuth trisneodecanoate and other bismuth carboxylates; zirconium compounds or aluminum compounds, such as zirconium chelates and aluminum chelates; dialkyltin dicarboxylates, such as dibutyltin dilaurate and dibutyltin acetate, tertiary amines, the stannous salts of carboxylic acids, such as stannous octoate and stannous acetate, and the like.

In a second process step, the isocyanate-terminated prepolymer of general Formula (4) is reacted with silane(s) that contain an active hydrogen functional group to prepare moisture-curable polymer (a). The silanes that contain an active hydrogen-functional group are provided by the general Formula (5):

$$HA^2R^7-SiX^1X^2X^3 \quad (5)$$

wherein $R^7$ is independently a divalent hydrocarbylene group containing from 1 to 12 carbon atoms selected from the group consisting of divalent alkylene, alkenylene, arenylene, arylene and aralkylene, and, optionally, contains at least one heteroatom selected from the group consisting of oxygen and sulfur; each occurrence of $A^2$ is independently selected from the group consisting of oxygen (—O—), sulfur (—S—), (-)$_2$NR$^8$, —NR(C=O)NR$^8$—, —NR$^8$(C=O)O— and —NR$^8$(C=O)S—, wherein $R^8$ is hydrogen, alkyl, alkenyl, arenyl, aralkyl or —R$^7$SiX$^1$X$^2$X$^3$ group, wherein each $R^8$, other than hydrogen, contains from 1 to 18 carbon atoms; and $X^1$, $X^2$ and $X^3$ have the aforestated meanings.

The silane terminating reactions of the present invention can be any kind as known in the art, e.g., those reactions disclosed in U.S. Pat. No. 6,197,912 and U.S. Pat. No. 5,990,257, the entire contents of which are incorporated herein by reference.

The active hydrogen organofunctional silanes include, e.g., primary and secondary amino-alkoxysilanes, ureido-alkoxysilane, carbamatosilane, thiocarbamatosilane and mercaptoalkoxysilanes. Representative examples of suitable aminosilanes include, but are not limited to, N-phenyl-aminomethyltrimethoxysilane, N-cyclohexyl-aminomethyl-trimethoxysilane, aminomethyltrimethoxysilane, N-phenyl-3-aminopropyltrimethoxysilane, N-methyl-3-aminopropyltrimethoxysilane, N-butyl-3-aminopropyltrimethoxysilane, 4-amino-3,3-dimethylbutyltrimethoxysilane, N-cyclohexyl-3-aminopropyltrimethoxysilane, dibutyl maleate adduct of 3-aminopropyltrimethoxysilane, dibutyl maleate adduct of 4-amino-3,3-dimethylbutyltrimethoxysilane, 3-aminopropyltriethoxysilane, bis-(3-trimethoxysilylpropyl) amine, 3-aminopropylmethyldimethoxysilane, 3-aminopropyldimethyl(methylethyloximato)silane, N-methyl-3-amino-2-methylpropyltrimethoxysilane, N-ethyl-3-amino-2-methylpropyltrimethoxysilane, N-ethyl-3-amino-2-methylpropyldiethoxymethylsilane, N-ethyl-3-amino-2-methylpropyltriethoxysilane, N-ethyl-3-amino-2-methylpropylmethyldimethoxysilane, N-butyl-3-amino-2-methylpropyltrimethoxysilane, 3-(N-methyl-2-amino-1-methyl-1-ethoxy)propyltrimethoxysilane, N-ethyl-4-amino-3,3-dimethylbutyldimethoxymethylsilane, N-ethyl-4-amino-3,3-dimethylbutyltrimethoxysilane, bis-(3-trimethoxysilyl-2-methylpropyl)amine, N-(3'-trimethoxysilylpropyl)-3-amino-2-methylpropyltrimethoxysilane, 3-mercaptopropyltrimethoxysilane, 3-mercaptopropyltriethoxysilane, 3-mercaptopropylmethyldimethoxysilane, 3-ureidopropyltrimethoxysilane, 3-ureidopropylmethyldimethoxysilane, O-(3-trimethoxysilylpropyl) carbamate and mixtures thereof.

Synthetic Method 2: Reaction of a Polyol with a Hydrolysable Silane Containing an Isocyanate-Functional Group to Provide a Moisture-Curable Polymer Containing at Least One Hydrolysable Silyl Group The above-mentioned hydroxyl-functional polyols are converted into moisture-curable polymer (a) in known manner by reaction with an isocyanate-functional silane. The moisture-curable polymer (a) is prepared by reacting a polyol or a combination of polyols usually in the presence of a catalyst with less than an equivalent to slightly more than an equivalent of hydrolysable silane containing an isocyanate group. The ratio of —NCO to —OH is specifically from 0.3 to 1.1, more specifically from 0.5 to 1, and most specifically from 0.95 to 0.99. When the ratio of —NCO to —OH is less than 1, the moisture-curable polymer (a) has residual hydroxyl groups, which may be advantages to improve adhesion to substrates.

Suitable hydrolysable silanes containing an isocyanate-functional group for use in preparing components (a), of the present invention, have the general Formula (6):

$$OCN-R^7-SiX^1X^2X^3 \quad (6)$$

wherein $R^7$ and $X^1$, $X^2$ and $X^3$ have the aforestated meanings.

Specific hydrolysable silanes containing an isocyanate-functional group, as represented by general Formula (6), that are suitable for use herein include, but not limited to, isocyanatomethyltrimethoxysilane, isocyanatomethylmethyldimethoxysilane, 3-isocyanatopropyltrimethoxysilane, 3-isocyanatoisopropyltrimethoxysilane, 4-isocyanatobutyltrimethoxysilane, 2-isocyanato-1,1-dimethylethyltrimethoxysilane, 3-isocyanatopropyltriethoxysilane, 3-isocyanatoisopropyltriethoxysilane, 4-isocyanatobutyltriethoxysilane, 2-isocyanato-1,1-dimethylethyltriethoxysilane, 3-isocyanatopropylmethyldimethoxysilane, 3-isocyanatoisopropyldimethylmethoxysilane, 4-isocyanatobutylphenyldimethoxysilane, 2-(4-isocyanatophenyl)ethylmethyldimethoxysilane and the like.

Method 3: Reaction of Polyols with Ethylenically Unsaturated Halo-Compounds and then Silanes Containing an Si—H Group to Provide a Moisture-Curable Polymer Containing at Least One Hydrolysable Silyl Group The above-mentioned hydroxyl-functional polyols are converted into ethylenically unsaturated prepolymers in known manner by reaction with ethylenically unsaturated halo compounds. These prepolymers are prepared by reacting less than equivalent amounts of ethylenically unsaturated halo compounds with a polyol or a combination of polyols usually in the presence of a catalyst.

The ethylenically unsaturated halo compounds useful in the preparation of the ethylenically unsaturated polymers are provided by general Formula (7):

$$Y^1R^{11}C(R^2)\!=\!CH_2 \qquad (7)$$

wherein $R^{11}$ is a divalent hydrocarbylene group containing from 1 to 10 carbon atoms selected from the group consisting of divalent alkylene, alkenylene, arenylene, arylene and aralkylene, and, optionally, contains at least one heteroatom selected from the group consisting of oxygen and sulfur; $R^{12}$ is a hydrogen or an alkyl group of from 1 to 6 carbon atoms; and each $Y^1$ is independently a halogen atom, selected from the group consisting of Cl—, Br— and I—. The reaction conditions are well known in the art, as for example U.S. Pat. Nos. 3,951,888 and 3,971,751, the entire content of which are incorporated herein by reference.

Representative non-limiting examples of ethylenically unsaturated halogen compounds, as represented by general Formula (7), include allyl chloride, allyl bromide, allyl iodide, methallyl chloride, methallyl bromide, 6-chlorohexene, chloromethylstyrene, and the like.

In the final step, the ethylenically unsaturated prepolymer is hydrosilated with hydrolysable hydridosilane of Formula (8):

$$HSiX^1X^2X^3 \qquad (8)$$

wherein $X^1$, $X^2$ and $X^3$ have the aforestated meanings. The conditions for hydrosilation of intermediates containing carbon-carbon double bonds is well known in the art, such as described in "Comprehensive Handbook of Hydrosilylation, "B. Marciniec (ed), Pergamon Press, New York (1992), which is included in its entirety herein by reference.

Useful hydrolysable hydridosilanes include, but are not limited to, H—Si(OCH$_3$)$_3$, H—Si(OCH$_2$CH$_3$)$_3$, H—SiCH$_3$(OCH$_3$)$_3$, H—SiCH$_3$(OCH$_2$CH$_3$)$_2$, H—Si(CH$_3$)$_2$OCH$_3$, H—Si(CH$_3$)$_2$OCH$_2$CH$_3$, and the like.

Preferably, moisture-curable polymer (a) is provided by Formula (3) wherein $R^6$ is a polymer specifically having a number average molecular weight from 500 to 25,000 grams per mole, more specifically from 1,000 to 20,000 grams per mole and most specifically from 4,000 to 12,000 grams per mole. The flexibility of the cured moisture curable polymer (a) is improved when the Tg is from −20° C. to −80° C., more specifically from −25° C. to −40° C. and most specifically from −30° C. to −35° C. Preferably, $R^7$ is an alkylene or arylene of from 1 to 6 carbon atoms, more preferably from 1 to 3 carbon atoms and most preferably 3 carbon atoms; $A^1$ is oxygen or substituted nitrogen of the structure (–)$_2$NR$^8$, wherein R$^8$ is specifically hydrogen, alkyl or aryl, wherein each R$^8$, other than hydrogen, contains specifically 1 to 10 carbon atoms and more specifically, 1 to 6 carbon atoms; $A^2$ is substituted nitrogen of the structure (–)$_2$NR$^8$, wherein R$^8$ is specifically hydrogen, alkyl or aryl, wherein each R$^8$, other than hydrogen, contains specifically 1 to 10 carbon atoms and more specifically, 1 to 6 carbon atoms; $X^1$ and $X^2$ are methoxy, ethoxy or propoxy; and $X^3$ is methyl, methoxy, ethoxy or propoxy.

Representative examples of moisture-curable polymers (a) include, but are not limited to, polymer from Momentive Performance Materials, Inc., sold under the trade names SPUR 1010, 1015 and 1050, which are trimethoxysilyl-terminated polypropylene oxide based polyurethanes of different molecular weights.

The moisture-curable polymer (a) may be present in the composition in an amount of from 30 weight percent to 90 weight percent based on the total weight of components (a), (b) and (c), preferably in an amount of from 50 weight percent to 90 weight percent based on the total weight of components (a), (b) and (c), and more preferably, in an amount of from 60 weight percent to 80 weight percent based on the total weight of components (a), (b) and (c).

As used herein, the term "reactive modifier" refers to a compound containing a hydrolysable silyl group that, when combined with a moisture-curable polymer having at least one hydrolysable silyl group, lowers the viscosity and increases the modulus of a resulting cured silylated polymer composition compared to a cured silylated polymer composition not containing the reactive modifier.

The reactive modifier (b) is a compound of the general Formula (1) or (2):

$$G^1[-R^1SiR^2_a(OR^3)_{3-a}]_b \qquad \text{(Formula 1); and}$$

$$G^2[-SiR^4_c(OR^5)_{3-c}]_d \qquad \text{(Formula 2)}$$

wherein:

$G^1$ is selected from the group consisting of a divalent or polyvalent cyclic hydrocarbon group containing from 5 to 16 carbon atoms, a divalent or polyvalent cyclic heterocarbon group containing from 3 to 16 carbon atoms wherein the heteroatoms are selected from the group consisting of oxygen, silicon and sulfur; and a divalent or polyvalent cyclic silicone group containing from 3 to 8 silicon atoms and from 3 to 8 oxygen atoms;

$G^2$ is selected from the group consisting of a monovalent or divalent linear hydrocarbon group containing from 3 to 16 carbon atoms; and a monovalent or divalent linear heterocarbon containing from 3 to 16 carbon atoms wherein the heteroatom are selected from the group consisting of oxygen, silicon and sulfur;

each occurrence of $R^1$ is independently selected from the group consisting of a covalent bond between the silicon atom and $G^1$, a divalent hydrocarbon group containing from 1 to 18 carbon atoms, and optionally at least one heteroatom selected from the group consisting of oxygen, silicon and sulfur;

each occurrence of $R^2$ is monovalent hydrocarbon containing from 1 to 12 carbon atoms;

each occurrence of $R^3$ is monovalent hydrocarbon containing from 1 to 12 carbon atoms;

each occurrence of $R^4$ is monovalent hydrocarbon containing from 1 to 12 carbon atoms;

each occurrence of $R^5$ is monovalent hydrocarbon containing from 1 to 12 carbon atoms;

each occurrence of a, b, c and d is independently an integer, wherein a is 0 to 2; b is 2 to 6; c is 0 to 2; and d is 1 or 2 with the provisos that (i) when $R^1$ is a chemical bond, then the silicon atom is covalently bonded to a carbon atom of $G^1$;

(ii) when $R^1$ contains a heteroatom, the silicon atom is bonded to a carbon atom of $R^1$;

(iii) when $G^2$ contains a heteroatom, the terminal atoms of $G^2$ are carbon atoms; and (iv) when the silicon atom is attached to $G^2$, the silicon atom is covalently bonded to a terminal carbon of $G^2$.

In connection with the reactive modifier (b) of Formula (1), $G^2$ may be a divalent or polyvalent cyclic hydrocarbon groups include "cyclic aliphatic" and aryl groups. Cyclic aliphatic groups are derived from cyclic aliphatic hydrocarbons from which two or more hydrogen atoms have been removed and can contain one or more carbon-carbon double bonds; and "aryl" groups are derived from aromatic hydrocarbon from which two or more hydrogen atoms have been removed. These cyclic hydrocarbon groups can be monocyclic, bicyclic or polycyclic groups.

Specific and non-limiting examples of cyclic aliphatic hydrocarbons from which the $G^1$ group is derived include cyclopentane, cyclohexane, cycloheptane, cyclooctane, cyclooctatriene, cyclododocane, norbornane, norbornene, cyclododecatriene and the like. Specific and non-limiting examples of cyclic aromatic hydrocarbons from which the $G^1$ group is derived include benzene, toluene, xylene, napthalene, ethylbenzene, and the like. Specific and non-limiting cyclic heteroatom ring structures from which $G^1$ group is derived include, tetrahydrofuran, furan, tetrahydrothiophene, [1,4]-dioxane, 1,3-bis-(2-cyclohexyl-ethyl)-1,1,3,3-tetramethyl-disiloxane, 2,2,4,4,6,6-hexamethyl-[1,3,5,2,4,6]-trioxatrisilinane, and the like. Specific and non-limiting examples of cyclic silicones from which the $G^1$ group is derived include 2,2,4,6-tetramethyl-[1,3,5,2,4,6]trioxatrisilinane, 2,4,6-trimethyl-[1,3,5,2,4,6]trioxatrisilinane, 2,4,6,8-tetramethyl-[1,3,5,7,2,4,6,8]tetroxatetrasilocane, 2,2,4,6,8-pentamethyl-[1,3,5,7,2,4,6,8]tetroxatetrasilocane, 2,2,4,4,6,8-hexamethyl-[1,3,5,7,2,4,6,8]tetroxatetrasilocane and the like.

In connection with the reactive modifier (b) of Formula (2), monovalent and divalent linear hydrocarbon group containing from 3 to 16 carbon atoms; and a monovalent or divalent linear heterocarbon containing from 3 to 16 carbon atoms wherein the heteroatom are selected from the group consisting of oxygen, silicon and sulfur. The monovalent linear hydrocarbon groups include, alkyl and alkenyl. Divalent linear hydrocarbon groups include, alkylene and alkenylene. Divalent heterocarbon groups include alkylene groups containing at least one oxygen, silicon or sulfur atom and terminal carbon atoms.

Specific and non-limiting examples of linear monovalent and divalent hydrocarbons from which the $G^2$ group is derived include pentane, hexane, heptane, octane, decane, dodecane, hexadecane, and the like. Specific and non-limiting examples of linear divalent heteroatoms from which the $G^2$ is derived include dipropylether, 3,5-dioxadecane, dipropylthio ether, dipropyldisulfide, dipropyltetrasulfide, and the like.

Reactive modifiers (b) of the present invention may be prepared by various methods known in the art. In one method, the reactive modifiers are prepared by reacting a divalent or polyvalent cyclic organic group containing at least two alkenyl groups, i.e. groups that contain a carbon-carbon double bond, with a hydrolysable hydridosilane of Formula (8):

$$HSiX^1X^2X^3 \qquad (8)$$

wherein $X^1$, $X^2$ and $X^3$ have the aforestated meanings. The conditions for hydrosilation of intermediates containing carbon-carbon double bonds is well known in the art, such as described in "Comprehensive Handbook of Hydrosilylation, "B. Marciniec (ed), Pergamon Press, New York (1992), which is included in its entirety herein by reference.

Representative, non-limiting examples of the reactive modifiers (b) include, but are not limited to, 1,2,4-tris-[2-(trimethoxy-silanyl)-ethyl]-cyclohexane, 1,2,4-tris-[2-(dimethoxy-methyl-silanyl)-ethyl]-cyclohexane, 1,2,4-tris-[2-(triethoxy-silanyl)-ethyl]-cyclohexane, 1,2,4-tris-[2-(tripropoxy-silanyl)-ethyl]-cyclohexane, 1,4-bis-[2-(trimethoxy-silanyl)-ethyl]-2-vinyl-cyclohexane, 1,4-bis-[2-(dimethoxy-methyl-silanyl)-ethyl]-2-vinyl-cyclohexane, 1,4-bis-[2-(triethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, 1-(2-{2,5-bis-[2-(dimethoxy-methyl-silanyl)-ethyl]-cyclohexyl}-ethyl)-3-(2-{2,4-bis-[2-(dimethoxy-methyl-silanyl)-ethyl]-cyclohexyl}-ethyl)-1,1,3,3-tetramethyl-disiloxane, 1-(2-{2,5-bis-[2-(triethoxy-silanyl)-ethyl]-cyclohexyl}-ethyl)-3-(2-{2,4-bis-[2-(triethoxy-silanyl)-ethyl]-cyclohexyl}-ethyl)-1,1,3,3-tetramethyl-disiloxane, 2,5-bis-[2-(trimethoxy-silanyl)-ethyl]-bicyclo[2.2.1]heptane, 2,5-bis-[2-(dimethoxy-methyl-silanyl)-ethyl]-bicyclo[2.2.1]heptane, 2,5-bis-[2-(triethoxy-silanyl)-ethyl]-bicyclo[2.2.1]heptane, 1-(2-{6-[2-(trimethoxy-silanyl)-ethyl]-bicyclo[2.2.1]hept-2-yl}-ethyl)-3-(2-{5-[2-(trimethoxy-silanyl)-ethyl]-bicyclo[2.2.1]hept-2-yl}-ethyl)-1,1,3,3-tetramethyl-disiloxane, 1-(2-{6-[2-(dimethoxy-methyl-silanyl)-ethyl]-bicyclo[2.2.1]hept-2-yl}-ethyl)-3-(2-{5-[2-(dimethoxy-methyl-silanyl)-ethyl]-bicyclo[2.2.1]hept-2-yl}-ethyl)-1,1,3,3-tetramethyl-disiloxane, 1-(2-{6-[2-(triethoxy-silanyl)-ethyl]-bicyclo[2.2.1]hept-2-yl}-ethyl)-3-(2-{5-[2-(triethoxy-silanyl)-ethyl]-bicyclo[2.2.1]hept-2-yl}-ethyl)-1,1,3,3-tetramethyl-disiloxane, 1,4-bis-[2-(trimethoxy-silanyl)-ethyl]-benzene, 1,4-bis-[2-(dimethoxy-methyl-silanyl)-ethyl]-benzene, 1,4-bis-[2-(triethoxy-silanyl)-ethyl]-benzene, 2,4,6,8-tetrakis-[2-(trimethoxy-silanyl)-ethyl]-2,4,6,8-tetramethyl-[1,3,5,7,2,4,6,8]tetroxatetrasilocane, 2,4,6,8-tetrakis-[2-(dimethoxy-methyl-silanyl)-ethyl]-2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(dimethoxy-methyl-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, trimethoxy-pentyl-silane, dimethoxy-methyl-pentyl-silane, triethoxy-hexyl-silane, trimethoxy-hexyl-silane, dimethoxy-methyl-hexyl-silane, triethoxy-hexyl-silane, trimethoxy-octyl-silane, dimethoxy-methyl-octyl-silane, triethoxy-octyl-silane, trimethoxy-hexadecyl-silane, dimethoxy-methyl-hexadecyl-silane, triethoxy-hexadecyl-silane, 1-(trimethoxy-silanyl)-3-[3-(trimethoxy-silanyl)-propylsulfanyl]-propane, 1-(dimethoxy-methyl-silanyl)-3-[3-(dimethoxy-methyl-silanyl)-propylsulfanyl]-propane, 1-(triethoxy-silanyl)-3-[3-(triethoxy-silanyl)-propylsulfanyl]-propane, 1-(trimethoxy-silanyl)-3-[3-(trimethoxy-silanyl)-propyldisulfanyl]-propane, 1-(dimethoxy-methyl-silanyl)-3-

[3-(dimethoxy-methyl-silanyl)-propyldisulfanyl]-propane, 1-(trimethoxy-silanyl)-3-[3-(trimethoxy-silanyl)-propyltetrasulfanyl]-propane, 1-(trimethoxy-silanyl)-3-[3-(trimethoxy-silanyl)-propyltetrasulfanyl]-propane, 1-(dimethoxy-methyl-silanyl)-3-[3-(dimethoxy-methyl-silanyl)-propyletrasulfanyl]-propane, 1-(triethoxy-silanyl)-3-[3-(triethoxy-silanyl)-propyltetrasulfanyl]-propane, 1,8-bis-(trimethoxy-silanyl)-hexane, 1,8-bis-(dimethoxy-methyl-silanyl)-hexane, 1,8-bis-(triethoxy-silanyl)-hexane, 1,8-bis-(trimethoxy-silanyl)-octane, 1,8-bis-(dimethoxy-methyl-silanyl)-octane, 1,8-bis-(triethoxy-silanyl)-octane, 1-[2-(trimethoxy-silanyl)-ethyl]-3-[3-(trimethoxy-silanyl)-propyl]-1,1,3,3-tetramethyl-disiloxane, 1-[2-(dimethoxy-methyl-silanyl)-ethyl]3-[3-dimethoxy-methyl-silanyl)-propyl]-1,1,3,3-tetramethyl-disiloxane, 1-[2-(triethoxy-silanyl)-ethyl]-3-[3-(triethoxy-silanyl)-propyl]-1,1,3,3-tetramethyl-disiloxane, and combinations thereof.

In one embodiment, the reactive modifier (b) is selected from the group consisting of 1,2,4-tris-[2-(trimethoxy-silanyl)-ethyl]-cyclohexane, 1,2,4-tris-[2-(triethoxy-silanyl)-ethyl]-cyclohexane, 1,4-bis-[2-(trimethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, 2,5-bis-[2-(trimethoxy-silanyl)-ethyl]-bicyclo[2.2.1]heptane, 1,4-bis-[2-(trimethoxy-silanyl)-ethyl]-benzene, 2,4,6,8-tetrakis-[2-(trimethoxy-silanyl)-ethyl]-2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, trimethoxy-hexyl-silane, triethoxy-hexyl-silane, trimethoxy-octyl-silane, triethoxy-octyl-silane, 1-(trimethoxy-silanyl)-3-[3-(trimethoxy-silanyl)-propyldisulfanyl]-propane, 1-(triethoxy-silanyl)-3-[3-(triethoxy-silanyl)-propyldisulfanyl]-propane, 1-(trimethoxy-silanyl)-3-[3-(trimethoxy-silanyl)-propyltetrasulfanyl]-propane, 1-(trimethoxy-silanyl)-3-[3-(trimethoxy-silanyl)-propyltetrasulfanyl]-propane and 1-(triethoxy-silanyl)-3-[3-(triethoxy-silanyl)-propyltetrasulfanyl]-propane, and combinations thereof.

In another embodiment, the reactive modifier (b) is selected from the group consisting of 1,2,4-tris-[2-(triethoxy-silanyl)-ethyl]-cyclohexane, 2,4,6,8-tetrakis-[2-(triethoxy-silanyl)-ethyl]-2,4,6,8-tetramethyl-[1,3,5,7,2,4,6,8]tetroxatetrasilocane, triethoxy-octyl-silane, 1-(triethoxy-silanyl)-3-[3-(triethoxy-silanyl)-propyldisulfanyl]-propane and 1-(triethoxy-silanyl)-3-[3-(triethoxy-silanyl)-propyltetrasulfanyl]-propane, and combinations thereof.

The reactive modifier (b) may be present in the moisture-curable silylated polymer composition in an amount effective to lower the viscosity of a composition and increase the modulus of a cured composition for a particular application. In an embodiment, the reactive modifier (b) may be present in the composition in an amount of from 5 weight percent to 70 weight percent based on the total weight of components (a), (b) and (c), preferably in an amount of from 10 weight percent to 50 weight percent based on the total weight of components (a), (b) and (c) and most preferably in an amount of from 20 weight percent to 40 weight percent based on the total weight of components (a), (b) and (c).

The catalyst (c) of the moisture-curable composition can be any catalyst that is effective in promoting the reaction between moisture-curable polymer (a) and the reactive modifier (b), which occurs upon exposure to moisture. Suitable cure catalysts include but not limited to organometallic catalysts, amine catalysts, and the like. Preferably, the catalyst is selected from the group consisting of organic dibutyltin, zirconium complex, aluminum chelate, titanic chelate, organic zinc, organic cobalt, organic iron, organic nickel and organobismuth, and mixtures thereof. Amine catalysts are selected from the group consisting of primary amine, secondary amine, tertiary amine and aminosilane and mixtures thereof. The catalyst can be a mixture of organometallic catalyst and amine catalyst.

Representative examples of catalysts include, but are not limited to, dibutyltin oxide, dibutyltin dilaurate, dioctyltin dilaurate, dibutyltin diacetate, stannous octoate, stannous acetate, stannous oxide, morpholine, 3-aminopropyltrimethoxysilane, 2-(aminoethyl)-3-aminopropyltrimethoxysilane, tri-isopropylamine, bis-(2-dimethylaminoethyl) ether and piperazine. Other useful catalysts include zirconium-contain, aluminum-containing and bismuth-contain complexes such as KAT™ XC6212, K-KAT™ 5218 and K-KAT™ 348, supplied by King Industries, Inc., titanium chelates such as the TYZOR® types, available from DuPont, the KR™ types, available from Kenrich Petrochemical, Inc., amines such as NIAX™ A-501 amine, available from Momentive Performance Materials, Inc., and the like.

The catalyst may be present in the moisture-curable composition in an amount of from 0.05 weight percent to 5 weight percent based on the total weight of components (a), (b) and (c), preferably in an amount of from 0.1 weight percent to 3 weight percent based on the total weight of components (a), (b) and (c) and most preferably, in an amount of from 0.5 weight percent to 2 weight percent based on the total weight of components (a), (b) and (c).

For practical application, the moisture-curable composition may optionally contain additives, such as pigments, fillers, curing catalysts, dyes, plasticizers, thickeners, coupling agents, extenders, volatile organic solvents, wetting agents, tackifiers, crosslinking agents, thermoplastic polymers, and UV stabilizers. The typical additives may be used in the quantities familiar to a skilled person in the field.

Typical fillers suitable for formulation of the moisture-curable resin composition of the present invention include, for example, reinforcing fillers such as fumed silica, precipitated silica, clays, talc, aluminum silicates, calcium carbonates and the like. The plasticizers customarily employed in the moisture-curable resin composition of the present invention can also be used in the invention to modify the properties and to facilitate use of higher filler levels. Exemplary plasticizers include phthalates, diproplyene and diethylene glycol dibenzoates, alkylsulphonate phenols, alkyl phenathres, alkyl/diaryl phosphates and mixtures thereof and the like. The moisture-curable resin composition of the present invention can include various thixotropic or anti-sagging agents. Various castor waxes, fumed silica, treated clays and polyamides typify this class of additives. Stabilizers can be incorporated into the moisture-curable resin composition of this invention include, for example, hindered amine and dialkylhydroxyamine. Adhesion promoters are useful in the moisture-curable composition of the present invention, e.g., alkoxysilane adhesion promoters.

Thermoplastic polymers can be selected from among any of numerous polymers of the addition and condensation types inclusive of homopolymers, copolymers of two or more copolymerizable monomers and mixtures of two or more such polymers. Thermoplastic polymer (i) advantageously possesses a melt flow index of from 10 to 500 grams per 10 minutes, preferably from 150 to 450 grams per 10 minutes and more preferably from 200 to 400 grams per 10 minutes. Examples of suitable thermoplastic polymers are as follows:

1. Polymers of monoolefins and diolefins, e.g., polypropylene, polyisobutylene, polybut-1-ene, poly-4-methylpent-1-ene, polyisoprene or polybutadiene, as well as polymers of cycloolefins, e.g., of cyclopentene or norbornene, polyethylene (optionally crosslinked), e.g., high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE). Polyolefins, i.e., the polymers of monoolefins such as those aforementioned and preferably polyethylene and polypropylene, can be prepared by such methods as radical polymerization (normally under high pressure and at elevated temperature) and catalytic polymerization employing a catalyst typically containing one or more metals of groups IVb, Vb, VIb or VIII of the Periodic Table. These metals usually have one or more than one ligand, typically oxides, halides, alcoholates, esters, ethers, amines, alkyls, alkenyls and/or aryls that may be either p-or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).
2. Mixtures of the polymers mentioned under (1), e.g., mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, e.g., ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norborene; and mixtures of such copolymers with one another and with polymers mentioned in (1), supra, e.g., polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, e.g., polyamides.
4. Hydrocarbon resins (for example $C_5$-$C_9$) including hydrogenated modifications thereof and mixtures of polyalkylenes and starch.
5. Polystyrene, poly(p-methylstyrene), poly($\alpha$-methylstyrene).
6. Copolymers of styrene or a-methylstyrene with dienes or acrylic derivatives, e.g., styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymer and another polymer such as a polyacrylate, a diene polymer or an ethylene/propylene/diene terpolymer, and block copolymers of styrene such as styrene/butadiene/styrene, styrene/isoprene/styrene, styrene/ethylene/butylene/styrene and styrene/ethylene/propylene/styrene.
7. Graft copolymers of styrene or a-methylstyrene such as styrene on polybutadiene, styrene on polybutadiene-styrene or polybutadiene-acrylonitrile copolymers: styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under (6), e.g., the copolymer mixtures known as ABS, MBS, ASA or AES polymers.
8. Halogen-containing polymers such as polychloroprene, chlorinated rubbers, chlorinated and brominated copolymers of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds such as polyvinyl chloride, polyvinylidene chloride, polyvinyl fluoride, polyvinylidene fluoride and copolymers thereof such as vinyl chloride/vinylidene chloride, vinyl chloride/vinyl acetate or vinylidene chloride/vinyl acetate copolymers.
9. Polymers derived from alpha, beta-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under (9) with each other or with other unsaturated monomers such as acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins such as those mentioned in (1) above.

12. Homopolymers and copolymers of cyclic ethers such as polyalkylene glycols, polyethylene oxide, polypropylene oxide, and copolymers thereof with bisglycidyl ethers.
13. Polyacetals such as polyoxymethylene and those polyoxymethylenes derived from ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from the reaction of hydroxyl-terminated polyethers, polyesters or polybutadienes with aliphatic or aromatic polyisocyanates, as well as precursors thereof.
16. Polyamides and copolyamides derived from diamines and dicarboxylic acids and/or from aminocarboxylic acids or the corresponding lactams, for example polyamide 4, polyamide 6, polyamides 6/6, 6/10, 6/9, 6/12, 4/6 and 12/12, polyamide 11, polyamide 12, aromatic polyamides obtained from m-xylene diamine and adipic acid; polyamides obtained from hexamethylenediamine and isophthalic or/and terephthalic acid and with or without an elastomer as modifier, e.g., poly-2,4,4,-trimethylhexamethylene terephthalamide or poly-m-phenylene isophthalamide; block copolymers of the aforementioned polyamides with polyoletins, olefin copolymers, ionomers or chemically bonded or grafted elastomers; or with polyethers, e.g., with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.

Representative non-limiting examples of some commercially available thermoplastic polymers include atactic polypropylene copolymers available under the REXTAC™ series of trade designations including REXTAC™ RT 2535 and RT 2585 (Rexene Products Company) and EASTOFLEX™ series of trade designations including EASTOFLEX™ E1060 (Eastman Chemical Company); ethylene vinyl acetate copolymers available under the ELVAX series of trade designations including ELVAX™ 420 and 2609 (DuPont), and ULTRATHENE™ series of trade designations including ULTRATHENE™ 7710 (Millennium Petrochemicals); ethylene methyl acrylate copolymers available under the OPTEMA™ series of trade designations (Exxon Chemical Company); ethylene n-butyl acrylate copolymers available under the LOTRYL™ series of trade designation (Elf Atochem North America), the ESCORENE™ series of trade designations including ethylene vinyl acetate copolymer UL 7710 (Exxon Chemical Company) and the ENA-THENE™ series of trade designations (Millennium Petrochemicals); ethylene n-butyl acrylate carbon monoxide terpolymers available under the ELVALOY™ series of trade designations (DuPont); ethylene acrylic copolymers available under the ELVALOY™ series of trade designations (DuPont); and, acrylic polymers available under the ELVACITE™ series of trade designations (ICI Acrylics).

Tackifying agents (tackifiers) are substances that may be added to adhesive compositions to improve their initial and extended tack range. A preferred group of tackifying agents are hydrocarbons containing from 6 to 10,000 carbon atoms, optionally containing at least one oxygen atom, and having a ring and ball softening point of from 70 to 120° C. and preferably from 80 to 100° C. Suitable tackifying agents herein are aliphatic, cycloaliphatic, aromatic, aliphatic-aromatic, aromatic-modified alicyclic and alicyclic hydrocarbon resins and hydrogenated derivatives thereof; terpenes, polyterpenes and modified terpenes such as phenolic-modified terpene resins and hydrogenated derivatives thereof; natural and modified rosin, hydrogenated rosin, dimerized rosin and polymerized rosin; rosin esters such as the glycerol and pentaerythritol esters of natural and modified rosins, glycerol esters of fatty organic acids, wood rosins, glycerol esters of hydrogenated rosin, glycerol esters of polymerized rosin, pentaerythritol esters of hydrogenated rosin and phenolic-modified pentaerythritol esters of rosin; alpha-methyl styrene resins and hydrogenated derivatives thereof; and, low molecular weight polylactic acid. Other useful tackifying agents are those disclosed in U.S. Pat. No. 6,355,317, the entire contents of which are incorporated by reference herein.

Representative non-limiting examples of specific tackifying resins that can be used herein include partially hydrogenated cycloaliphatic petroleum hydrocarbon resins available under the EASTOTAC™ series of trade designations such as EASTOTAC™ H-100, H-115, H-130 and H-142 in grades E, R, L and W which have differing levels of hydrogenation from least hydrogenated (E) to most hydrogenated (W) (Eastman Chemical Company), the ESCOREZ™ series of trade designations, such as ESCOREZ 5300 and ESCOREZ 5400 (Exxon Chemical Company), and the HERCOLITE™ 2100 trade designation (Hercules); partially hydrogenated aromatic modified petroleum hydrocarbon resins available under the ESCOREZ™ 5600 trade designation (Exxon Chemical Company); aliphatic-aromatic petroleum hydrocarbon resins available under the WINGTACK EXTRA trade designation (Goodyear Chemical Company); styrenated terpene resins made from d-limonene available under the ZONATAC™ 105 LITE trade designations (Arizona Chemical Company); and, aromatic hydrogenated hydrocarbon resins available under the REGAL-REZ™ 1094 trade designation (Hercules); and, alpha-methyl styrene resins available under the trade designations KRISTALEX™ 3070, 3085 and 3100 (Hercules).

In one embodiment of the present invention, the moisture-curable resin composition comprises from 50 weight percent to 90 weight percent of component (a), a moisture-curable polymer having at least one hydrolysable group, from 10 weight percent to 50 weight percent of component (b), a reactive modifier having the general Formula (1) or (2) as presented above, and from 0.1 weight percent to 3 weight percent of component (c), a catalyst for catalyzing the reaction between components (a) and (b) under curing conditions, all weight percentages based upon the total weight of components (a), (b) and (c), wherein $G^1$ is a divalent or polyvalent cyclic hydrocarbon containing from 6 to 10 carbon atoms; $G^2$ is a monovalent or divalent linear hydrocarbon containing from 6 to 12 carbon atoms, each occurrence of $R^1$ and $R^7$ is independently an alkylene group of from 1 to 6 carbon atoms; each occurrence of $R^2$, $R^3$, $R^4$, $R^5$, $R^9$ and $R^{10}$ is independently an alkyl group of from 1 to 4 carbon atoms; $R^8$ is hydrogen; each occurrence of $A^1$ is independently oxygen (—O—) or —$NR^8$—; each occurrence of $A^2$ is independently oxygen (—O—) or —$NR^8$—; a is 0 or 1; b is 2 or 3; c is 0 or 1; d is 1 or 2; e is 1 and f is 2.

In another embodiment of the present invention, the moisture-curable resin composition comprises from 60 weight percent to 80 weight percent of component (a), a moisture-curable polymer having at least one hydrolysable group, from 20 weight percent to 40 weight percent of component (b), a reactive modifier having the general Formula (1) or Formula (2) as presented above, and from 0.5 weight percent to 2 weight percent of component (c), a catalyst for catalyzing the reaction between components (a) and (b) under curing conditions, all weight percentages based upon the total weight of components (a), (b) and (c), wherein $G^1$ is a divalent or polyvalent cyclic hydrocarbon derivable from cyclohexane, cyclooctane and cyclodecane; $G^2$ is a monovalent or divalent linear hydrocarbon derivable from pentane, hexane, octane, decane, dodecane; each occurrence of $R^1$ and $R^7$ is independently methylene, ethylene or propylene; each occurrence of $R^2$, $R^3$, $R^4$, $R^5$, $R^9$ and $R^{10}$ is independently methyl or ethyl; $R^8$ is hydrogen; each occurrence of $A^1$ is independently oxygen (—O—) or —$NR^8$—; each occurrence of $A^2$ is independently oxygen (—O—) or —$NR^8$—; a is 0; b is 3; c is 0; d is 1; e is 1; and f is 2.

In yet another embodiment of the present invention, the moisture-curable resin composition comprises from 60 weight percent to 80 weight percent of component (a), a moisture-curable polymer having at least one hydrolysable group, from 20 weight percent to 40 weight percent of component (b), a reactive modifier (b) having the general Formula (1) or Formula (2) as presented above, and from 0.5 weight percent to 2 weight percent of component (c), a catalyst for catalyzing the reaction between components (a) and (b) under curing conditions, all weight percentages based upon the total weight of components (a), (b) and (c), wherein $G^1$ is a divalent or polyvalent cyclic hydrocarbon derivable from cyclohexane, cyclooctane and cyclodecane; $G^2$ is a monovalent or divalent linear hydrocarbon derivable from pentane, hexane, octane, decane, dodecane; each occurrence of $R^1$ and $R^7$ is independently methylene, ethylene or propylene; each occurrence of $R^2$, $R^3$, $R^4$, $R^5$, $R^9$ and $R^{10}$ is independently methyl or ethyl; $R^8$ is hydrogen; each occurrence of $A^1$ is independently oxygen (—O—); a is 0 or 1; b is 2 or 3; c is 0 or 1; d is 1 or 2; e is 0; and f is 2.

In still yet another embodiment of the present invention, the moisture-curable resin composition comprises from 1 weight percent to 25 weight percent of component (a), a moisture-curable polymer having at least one hydrolysable group, from 0.5 weight percent to 10 weight percent of component (b), a reactive modifier (b) having the general Formula (1) or Formula (2) as presented above, from 0.05 to 2 weight percent of a catalyst (c), from 25 weight percent to 80 weight percent of a thermoplastic polymer, and from 25 weight percent to 75 weight percent of a tackifier, all weight percentages based upon the total weight of components (a), (b), the thermoplastic polymer and the tackifier.

The moisture-curable resin composition of the invention may have a viscosity of less than 25,000 cP, specifically from a range of 500 cP to 20,000 cP, and more specifically from 2,000 cp to 15,000 cP without using any volatile organic solvents or using less than 25 weight percent of volatile organic solvents based upon the total weight of components (a), (b) and (c), as for example, from 1 to 10 weight percent of volatile organic solvents based upon the total weight of components (a), (b) and (c).

In another aspect, the present invention also relates to cured compositions produced from curing the aforementioned moisture-curable resin compositions and to sealants, including hot melt sealants, primers, adhesives including hot melt adhesives and coatings containing such cured compositions. Illustratively, the cured compositions include hot melt compositions. The term, "hot melt composition" as used herein, is a solid material at room temperature that melts upon heating for application to a substrate and resolidifies upon cooling to form a firm bond between the solid material and the substrate. Hot melt compositions include, but are not limited to, hot melt sealants and hot melt adhesives. The cured composition of the invention may be produced by contacting a moisture-curable composition with water, said moisture-curable composition comprising:

(a) a moisture-curable polymer having at least one hydrolysable silyl group;

(b) a reactive modifier of the general Formula (1) or Formula (2):

 (Formula 1); and

 (Formula 2)

wherein:

$G^1$ is selected from the group consisting of a divalent or polyvalent cyclic hydrocarbon group containing from 5 to 16 carbon atoms, a divalent or polyvalent cyclic heterocarbon group containing from 3 to 16 carbon atoms wherein the heteroatom are selected from the group consisting of oxygen, silicon and sulfur; and a divalent or polyvalent cyclic silicone group containing from 3 to 8 silicon atoms and from 3 to 8 oxygen atoms;

$G^2$ is selected from the group consisting of a monovalent or divalent linear hydrocarbon group containing from 3 to 16 carbon atoms; and a monovalent or divalent linear heterocarbon containing from 3 to 16 carbon atoms wherein the heteroatoms are selected from the group consisting of oxygen, silicon and sulfur;

each occurrence of $R^1$ is independently selected from the group consisting of a covalent bond between the silicon atom and $G^1$, a divalent hydrocarbon group containing from 1 to 18 carbon atoms, and optionally the divalent hydrocarbon group at least one heteroatom selected from the group consisting of oxygen, silicon and sulfur;

each occurrence of $R^2$ is monovalent hydrocarbon containing from 1 to 12 carbon atoms;

each occurrence of $R^3$ is monovalent hydrocarbon containing from 1 to 12 carbon atoms;

each occurrence of $R^4$ is monovalent hydrocarbon containing from 1 to 12 carbon atoms;

each occurrence of $R^5$ is monovalent hydrocarbon containing from 1 to 12 carbon atoms;

each occurrence of a, b, c and d is independently an integer, wherein a is 0 to 2; b is 2 to 6; c is 0 to 2; and d is 1 or 2 with the provisos that, (i) when $R^1$ is a chemical bond, then the silicon atom is covalently bonded to a carbon atom of $G^1$;

(ii) when $R^1$ contains a heteroatom, the silicon atom is bonded to a carbon atom of $R^1$;

(iii) when $G^2$ contains a heteroatom, the terminal atoms of $G^2$ are carbon atoms; and (iv) when the silicon atom is attached to $G^2$, the silicon atom is covalently bonded to a terminal carbon of $G^2$; and (c) a catalyst for catalyzing the reaction between the moisture-curable polymer (a) and reactive modifier (b) under moisture curing conditions. As used herein, the term "water" means atmospheric moisture, steam, liquid water, ice or water mixed with other organic compounds, such as organic solvents and is preferably atmospheric moisture. The effective amount of water is that amount sufficient to react with the hydrolysable silyl groups and effect the cure of the composition. Cured compositions of the invention advantageously have a Young's modulus of greater than 1.50 MPa, preferably from 2.00 MPa to 15 MPa and most preferably from 3.00 MPa to 10 MPa, while maintaining % elongation at break of at least 75 percent and preferably from 90 percent to 50 percent.

The following examples are intended to illustrate, but in no way limit the scope of the present invention. All parts and percentages are by weight and all temperatures are in degrees Celsius unless explicitly stated otherwise.

EXAMPLES

The chemical names of the reactive modifiers according to the present invention and the chemical names of compounds used in the comparative compositions are shown in Table 1.

TABLE 1

| Chemical name of the reactive modifiers | |
| --- | --- |
| Component | Chemical Name |
| 1 | 1,2,4-tris-[2-(trimethoxy-silanyl)-ethyl]-cyclohexane |
| 2 | 1,4-bis-[2-(trimethoxy-silanyl)-ethyl]-2-vinyl-cyclohexane |
| 3 | 1,4-bis-[2-(triethoxy-silanyl)-ethyl]-2-vinyl-cyclohexane |
| 4 | 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane |
| 5 | 2,5-bis-[2-(trimethoxy-silanyl)-ethyl]-bicyclo[2.2.1]heptane |
| 6 | 1-(2-{6-[2-(trimethoxy-silanyl)-ethyl]-bicyclo[2.2.1]hept-2-yl}-ethyl)-3-(2-{5-[2-(trimethoxy-silanyl)-ethyl]-bicyclo[2.2.1]hept-2-yl}-ethyl)-1,1,3,3-tetramethyl-disiloxane |
| 7 | 1,4-bis-[2-(trimethoxy-silanyl)-ethyl]-benzene |
| 8 | 1-(triethoxy-silanyl)-3-[3-(triethoxy-silanyl)-propyldisulfanyl]-propane |
| 9 | 2,4,6,8-tetrakis-[2-(trimethoxy-silanyl)-ethyl]-2,4,6,8-tetramethyl-[1,3,5,7,2,4,6,8]tetroxatetrasilocane |
| 10 | 2,4,6-tris-[2-(triethoxy-silanyl)-ethyl]-2,4,6-trimethyl-[1,3,5,2,4,6]trioxatrisilinane |
| 11 | triethoxy-octyl-silane |
| 12 | trimethoxy-hexadecyl-silane |
| 13 | trimethoxy-propyl-silane |
| Comparative 1 | trimethoxy-[2-(7-oxa-bicyclo[4.1.0.]hept-3-yl)-ethyl]-silane |
| Comparative 2 | (2-bicyclo[2.2.1]hept-5-en-2-yl-ethyl)-trimethoxy-silane |
| Comparative 3 | 1-(diethoxy-methyl-silanyl)-2-(triethoxy-silanyl)-ethane |
| Comparative 4 | bis-[3-(trimethoxy-silanyl)-propyl]-amine |
| Comparative 5 | trimethoxy-methyl-silane |
| Comparative 6 | isobutyl-trimethoxy-silane |
| Comparative 7 | isobutyl-triethoxy-silane |
| Comparative 8 | (6-methyl-heptyl)-trimethoxy-silane |
| Comparative 9 | No reactive modifier |

Example 1

Preparation of 1,2,4-tris-[2-(trimethoxy-silanyl)-ethyl]-cyclohexane, component 1

Into a 500 ml round-bottom flask, equipped with an addition funnel, thermometer, condenser and a magnetic stirrer, were charged 1,2,4-trivinylcyclohexane (50 grams, 0.31 mole, from Acros Organics) and platinum catalyst (10 ppm of $H_2PtCl_6$ solution from Sigma-Aldrich). The mixture was heated to 90° C. and dry air was bubbled into the reaction mixture. Trimethoxysilane (124 grams, 1.02 mole, from Momentive), was added to the flask using an addition funnel over a 70-minute period at such a rate as to maintain the reaction temperature at approximately 90° C. The reaction was recatalyzed with platinum catalysts (10 ppm of platinum-divinyltetramethyldisiloxane complex, containing 1.9% Pt, Karstedt's catalyst; see U.S. Pat. No. 377,452) and promoted with dried air sparge. The reaction was monitored using gas chromatography. After the reaction was complete, excess trimethoxysilane was removed by vacuum distillation. The final product is a clear yellow liquid.

Example 2

Preparation of 1,4-bis-[2-(trimethoxy-silanyl)-ethyl]-2-vinyl-cyclohexane, component 2

A 5 liter round-bottom flask, equipped with an addition funnel, thermocouple, condenser and a magnetic stirrer, were charged with trivinylcyclohexane (1390 grams, 8.6 moles) and platinum catalyst (25 ppm of platinum(0)-1,3-divinyl-1,1,3,3-tetramethyldisiloxane complex in xylenes from Aldrich). The mixture was heated to 110° C. and then trimethoxysilane (836 grams, 6.9 mole) was added drop wise while sparging dry air through the flask. To minimize the tris-hydrosilylation, more than 1 molar equivalent of trivinylcyclohexane was used relative to trimethoxysilane. The reaction was exothermic during the addition. The temperature was maintained at approximately 110° C. by blowing cool air along the side of the flask. After the addition, the reaction temperature was then maintained at approximately 110° C. for several additional hours. The reaction was monitored using gas chromatography. An inhibitor, 1,3,5-trimethyl-2,4,6-(3,5-di-tert-butyl-4-hydroxybenzyl)benzene was added into the flask. The products were vacuum distilled at a pressure below 1 torr to separate the desired product from other impurities. The 1,4-bis-[2-(trimethoxy-silanyl)-ethyl]-2-vinyl-cyclohexane was collected at temperature of 125° C. to 173° C.

Example 3

Preparation of 1,4-bis-[2-(triethoxy-silanyl)-ethyl]-2-vinyl-cyclohexane, component 3

Into a 5 liter round-bottom flask, equipped with an addition funnel, thermocouple, condenser and a magnetic stir were charged 1,2,4-trivinylcyclohexane (1390 g rams, 8.6 moles) and platinum catalyst (25 ppm of platinum (0)-1,3-divinyl-1,1,3,3-tetramethyldisiloxane complex in xylenes from Aldrich). The mixture was heated to 110° C. and triethoxysilane (1132 grams, 6.9 mole, from Momentive Performance Materials, Inc.) was added drop wise while sparging dry air through the flask. The reaction was exothermic during the addition. The reaction temperature was maintained at approximately 110° C. using a stream of cool air along the side of the flask. After the addition, the reaction was stirred an additional few hours at 110° C. The reaction was monitored using gas chromatography. The products were vacuum distilled at a pressure below 1 torr, to separate out dihydrosilation product, 1,4-bis-[2-(triethoxy-silanyl)-ethyl]-2-vinyl-cyclohexane and its stereoisomers from unreacted trivinylcylcohexane and monohydrosilation product.

Example 4

Preparation of 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, component 4

Into a 3 liter round bottom flask, equipped with an addition funnel, Friedrich condenser, thermocouple, stir bar and a nitrogen line were charged 1,4-bis-[2-(triethoxy-silanyl)-ethyl]-2-vinyl-cyclohexane (1072 grams, 2.9 moles, from Example 2) and platinum catalysts (1.27 grams, 100 ppm Pt, of 3 wt % solution of platinum(0)-1,3-divinyl-1,3-divinyl-1,1,3,3-tetramethyldisiloxane complex in xylenes). When the reaction mixture was heated up to 112° C., 1,1,3,3-tetramethyldisiloxane (194 grams, 1.45 moles, from Gelest Inc.) was added at a rate to maintain the reaction temperature between 112° C. and 119° C. The reaction mixture was recatalyzed with platinum catalysts (200 ppm Pt) and dry air was bubbled intermittently into the reaction mixture. All unreacted components were removed and the high molecular weight product was purified by Kugel distillation under vacuum.

Example 5

Preparation of 2,5-bis-[2-(trimethoxy-silanyl)-ethyl]-bicyclo[2.2.1]heptane, component 5

Into a three neck 3 liter round bottom flask fitted with a magnetic stir bar, Friedrich condenser, thermocouple, addition funnel and a nitrogen line were charged 5-vinyl-2-norbornene (544 grams, 4.53 moles, from Sigma-Aldrich) and platinum catalyst (18.4 grams, 250 ppm Pt, of 3 wt % solution of platinum(0)-1,3-divinyl-1,3-divinyl-1,1,3,3-tetramethyldisiloxane complex in xylenes). The reaction mixture was heated to 80° C. and trichlorosilane (1,227.3 grams, 9.05 moles, from Sigma-Aldrich) was added over eight hours using an addition funnel. The reaction temperature was maintained between 78° C. and 140° C. An additional amount of platinum catalyst (250 ppm Pt) was added to maintain the hydrosilylation reaction. The product mixture ratio was approximately 1:1 weight percent mono and bis silylated vinyl norbornene.

The reaction mixture was then charged into a 5 liter round bottom flask that was equipped with a 6-inch Vigaraux column, distillation head, addition funnel, magnetic stir bar, and thermocouple. A large excess of trimethylorthoformate and methanol (at 1:4 molar ratio) was added to the chlorosilylated vinyl norbornene mixture using an addition funnel at 65° C. under a reduced vacuum (160 mmHg). The hydrogen chloride formed during the reaction was removed and methanol-trimethylformate mixture was added until the chloride content was below 0.5 weight percent by titration. The mono and bis trimethoxysilylated vinyl noroborneine constituents were isolated by vacuum distillation at 88° C. and 3 mmHg and 133° C. to 155° C. at 2 mmHg respectively.

Example 6

Preparation of 1-(2-{6-[2-(trimethoxy-silanyl)-ethyl]-bicyclo[2.2.1]hept-2-yl}-ethyl)-3-(2-{5-[2-(trimethoxy-silanyl)-ethyl]-bicyclo[2.2.1]hept-2-yl}-ethyl)-1,1,3,3-tetramethyl-disiloxane, component 6

Into a three neck 3 liter round bottom flask fitted with a magnetic stir bar, Friedrich condenser, addition funnel, thermocouple and a nitrogen line were charged (2-bicyclo[2.2.1]hept-5-en-2-yl-ethyl)-trimethoxy-silane (600 grams, 2.71 mole, the Comparative 2 as described below) and platinum catalyst (1.13 grams, 100 ppm Pt, of 3 wt % solution of platinum(0)-1,3-divinyl-1,3-divinyl-1,1,3,3-tetramethyldisiloxane complex in xylenes). While the reaction flask was being heated, tetramethyldisiloxane (173 grams, 1.29 moles) was added using an addition funnel. The addition was started when the reaction temperature reached 108° C. The reaction temperature was maintained between 108° C. and 114° C. An additional platinum catalyst (40 ppm Pt) was added to recatalyze the mixture. All unreacted components were removed by vacuum distillation at greater than 105° C. and 4 mmHg pressure. The high molecular weight product was further purified using a Kugel distillation.

Example 7

Preparation of 1,4-bis-[2-(trimethoxy-silanyl)-ethyl]-benzene, component 7

Into a three neck 2 liter round bottom flask fitted with a magnetic stir bar, Friedrich condenser, addition funnel, thermocouple and a nitrogen line were charged divinylbenzene (400 grams, 3.07 moles, technical grade from PCI) and platinum catalyst (3.28 grams, 100 ppm Pt, of platinum(0)-1,3-divinyl-1,3-divinyl-1,1,3,3-tetramethyldisiloxane complex in xylenes). The reaction mixture was heated to a temperature of 74° C. at which time the addition trichlorosilane (745 grams, 5.5 moles) was initiated. The addition took approximately 90 minutes. The reaction mixture temperature was maintained between 74° C. and 107° C. All low boiling components were removed by vacuum after reaction was completed.

Into a three neck 3 liter round bottom flask fitted with a 6-inch Vigaraux distilling head, Claisen adapter, thermocouple, magnetic stirrer and addition funnel was charged 1,4-bis-[2-(trichloro-silanyl)-ethyl-benzene (724 grams, 1.8 moles). The silane was heated to 60° C. Ethanol 9498, 10.8 moles 0 was added drop wise under a vacuum of 60 mmHg pressure, followed by the addition of sodium ethoxide (2.5 grams) in ethanol (1618 grams, 35 moles). Excess ethanol was removed by distilling at pot temperature of 99° C. and 1 mmHg. The residual material was further purified using a Kugel distillation.

Example 8

Preparation of 2,4,6,8-tetrakis-[2-(trimethoxy-silanyl)-ethyl]-2,4,6,8-tetramethyl-[1,3,5,7,2,4,6,8]tetroxatetrasilocane, component 9

Vinyltrimethoxysilane (203 grams, 1.37 mole from Momentive Performance Materials, Inc.) was charged into a 500 mL round bottom flask equipped with a heating mantle, temperature controller, addition funnel, and a magnetic stirrer. The platinum catalysts (platinum(0)-1,3-divinyl-1,3- divinyl-1,1,3,3-tetramethyldisiloxane complex in xylenes, 10 ppm Pt) was added to the reactor. The reaction was heated to 80° C. and then 1,3,5,7-tetramethylcyclotetrasiloxane (75 grams, 0.31 mole from Gelest) was added drop wise over 30 minutes. The temperature was maintained by a water bath and did not exceed 105° C. After the addition, the reactor temperature was maintained at 80° C. for 16 hours. The product was transferred to a 1 liter single neck flask and stripped using a rotary evaporator for 1.5 hours at 7 torr and 100° C. The resulting fluid exhibited a viscosity of 46.8 Cst and was clear and nearly colorless.

Example 9

Preparation of 2,4,6-tris-[2-(triethoxy-silanyl)-ethyl]-2,4,6-trimethyl-[1,3,5,2,4,6]trioxatrisilinane, component 10

1,3,5-trivinyltrimethylcyclotrisiloxane (100 grams, 0.39 mole from Momentive Performance Materials, Inc.) was charged in a 500 mL round bottom flask equipped with a heating mantle, temperature controller, addition funnel, and a magnetic stirrer. Platinum catalysts (platinum(0)-1,3-divinyl-1,3-divinyl-1,1,3,3-tetramethyldisiloxane complex in xylenes, 15 ppm Pt) was added and the reaction mixture was heated to 80° C. Triethoxysilane (198 grams, 1.21 mole from Momentive Performance Materials, Inc.) was added drop wise over 2 hours using an addition funnel. Upon completion of the addition of triethoxysilane, the reactor temperature was maintained at 80° C. for 48 hours. The reaction was periodically monitored using gas chromatography. The product was transferred to a 1 liter single neck round bottom flask and stripped in a rotary evaporator at 1.2 torr and 75° C. for 1.5 hours. The resulting product was clear and nearly colorless.

Example 10

Preparation of (2-bicyclo[2.2.1]hept-5-en-2-yl-ethyl)-trimethoxy-silane, comparative component 2

Into a 5 liter round bottom flask, fitted with an addition funnel, Friedrich condenser, thermocouple, stir bar and nitrogen line, were charged 5-vinyl-2-norbornene (1500 grams, 12.48 moles, from Sigma-Aldrich), platinum catalyst (4.5 grams of a 3 wt % solution of platinum(0)-1,3-divinyl-1,3-divinyl-1,1,3,3-tetramethyldisiloxane complex in xylenes) and aniline (2.87 grams, 0.031 moles). The reaction mixture was heated gently to 100° C. and then trimethoxysilane (1372.5 grams, 11.23 moles from Momentive Performance Materials, Inc.) was incrementally charged into the flask. The reaction temperature was maintained using (controlling) the rate of addition and heating. The reaction mixture temperature was maintained in a ranged of from 63° C. to 118° C. The mixture was recatalyzed with an additional 1.3 grams of Pt complex and house air was bubbled intermittently into the reaction mixture using a small gage stainless steel needle introduced through a rubber septum. After all the trimethoxysilane had been consumed, the mixture was purified by vacuum distillation. The mono trimethoxysilylated product was isolated at 93° C. and 3 mmHg pressure leaving behind the bis trimethoxysilylated constituent.

Example 11

Preparation of Trimethoxysilyl-Terminated Polyurethane Polymer, Moisture Curable Polymer (a)

Into a four-neck reaction kettle was charged polypropylene glycol (1000 grams, 0.125 mole, weight average molecular weight of 8000 grams per mole from Bayer under the trade name Acclaim™ 8200 diol). The polyol was stirred and sparged with nitrogen gas at 60° C. for 16 hours. The temperature of the polyol was cooled to 45° C. and then isophorone diisocyanate (14.01 grams, 0.063 mole from Bayer) and tin catalyst (dibutyltin dilaurate, 7.5 ppm Sn, from Chemtura under the trade name Fomrez™ SUL-4) were added. After the isothermal had ceased, the reaction mixture was heated to 75° C. and maintained at this temperature with stirring and under a nitrogen gas blanket. The isocyanate content was checked every half hour using an n-butylamine titration method. When the isocyanate content was no longer detectable, 3-isocyanatopropyltrimethoxysilane (29.09 grams, 0.126 mole from Momentive Performance Materials, Inc.) was added and the reaction mixture was stirred at 75° C. until the isocyanate content was no longer detectable. The viscosity was approximately 40,000 cP at room temperature.

Examples 12-23 and Comparative Examples 1-9

Preparation of Moisture-Curable Resin Compositions, Curing and Mechanical Properties of the Cured Compositions A series of twenty-one compositions were prepared by blending the trimethoxysilyl-terminated polyurethane polymer, moisture curable polymer (a) from example 11 (80 grams), tin catalyst (0.8 grams of Fomrex™ UL 11A from Momentive Performance Materials, Inc.) and one of the reactive modifier components 1 to 12 or comparative components 1 to 9 (20 grams). Each mixture was stirred using a Speed Mixer DAC 400 for 30 second at 17,000 revolutions per minute (rpm). The mixture was a clear liquid having low viscosity. The mixture was then cast into a film and cured in a humidity chamber at 50% relative humidity and 35° C. for 10 days.

After cure, the mechanical properties of the moisture-curable resin compositions containing trimethoxysilyl-terminated polyurethane polymer (a) from example 11, Fomrex™ UL 11A catalyst (c) and one of the reactive modifier (b), components 1 to 12 or comparative components 1 to 9, were tested according to ASTM C 661 and D 412. All the results are listed in Table 2.

TABLE 2

Mechanical Properties of cured moisture-curable resin compositions

| Example | Reactive modifier component used in moisture-curable resin composition | Viscosity at 25° C. cP | Tensile Strength MPa (psi) | Young's Modulus MPa (psi) | Elongation (%) | Hardness Shore A |
|---------|---------|---------|---------|---------|---------|---------|
| 12 | 1 | 14,000 | 5.52 (801) | 7.43 (1078) | 98 | 62 |
| 13 | 2 | 11,000 | 4.26 (618) | 3.84 (557) | 155 | 50 |

TABLE 2-continued

Mechanical Properties of cured moisture-curable resin compositions

| Example | Reactive modifier component used in moisture-curable resin composition | Viscosity at 25° C. cP | Tensile Strength MPa (psi) | Young's Modulus MPa (psi) | Elongation (%) | Hardness Shore A |
|---|---|---|---|---|---|---|
| 14 | 3 | 11,000 | 4.95 (718) | 5.11 (741) | 131 | 47 |
| 15 | 4 | 13,000 | 3.02 (438) | 4.54 (658) | 85 | 66 |
| 16 | 5 | 14,000 | 3.59 (520) | 3.42 (496) | 136 | 40 |
| 17 | 6 | 11,700 | 2.81 (407) | 2.14 (311) | 153 | 41 |
| 18 | 7 | 14,000 | 3.16 (459) | 4.15 (603) | 97 | 58 |
| 19 | 8 | 13,000 | 2.88 (417) | 3.14 (456) | 113 | 35 |
| 20 | 9 | 12,000 | 3.61 (524) | 4.37 (634) | 96 | 47 |
| 21 | 10 | 11,000 | 2.72 (395) | 2.04 (296) | 177 | 41 |
| 22 | 11 | — | 2.07 (300) | 1.11 (161) | 238 | 34 |
| 23 | 12 | — | 1.60 (232) | 1.54 (224) | 185 | 41 |
| 24 | 13 | — | 1.24 (180) | 0.97 (140) | 205 | 29 |
| Comp. 1 | Comparative 1 | 11,900 | 0.39 (57) | 0.45 (65) | 159 | 20 |
| Comp. 2 | Comparative 2 | 18,400 | 0.40 (58) | 0.39 (56) | 265 | 14 |
| Comp. 3 | Comparative 3 | 7,600 | 1.60 (233) | 1.40 (203) | 137 | 42 |
| Comp. 4 | Comparative 4 | 9,900 | 1.38 (200) | 2.44 (354) | 66 | 43 |
| Comp. 5 | Comparative 5 | — | 0.99 (144) | 1.83 (265) | 165 | 36 |
| Comp. 6 | Comparative 6 | — | 0.96 (140) | 0.73 (106) | 260 | 21 |
| Comp. 7 | Comparative 7 | — | 0.85 (123) | 0.70 (102) | 236 | 22 |
| Comp. 8 | Comparative 9 | 40,000 | 0.49 (71) | 0.40 (58) | 215 | 18 |

From Table 2, it is seen that the employment of 20 weight percent of reactive modifiers (b) of the present invention in a moisture-curable composition containing polymer (a) and catalyst (c) significantly increase modulus and tensile strength of the cured moisture-curable resin compositions. Compared with a product made from a composition containing only silylated polyurethane and catalyst, Comparative Example 8, the moisture-curable resin compositions in examples 12-24 containing moisture-curable polymer (a), a reactive modifier (b) and catalyst (c) according to the present invention gain modulus and tensile strength by a factor of five times or more.

Another advantage of using the reactive modifiers according to the present invention is viscosity control. Results in Table 2 demonstrate that the products obtained from moisture-curable resin compositions, Examples 12-24, have viscosity much lower than the resin made from the composition that does not include any reactive modifiers (Comparative Example 8). This advantage is in favor of many adhesive applications.

The results also demonstrate that in order to gain the reinforcement, reactive modifiers must have at least two silane groups hydrosilated onto a polyvalent cyclic hydrocarbon or heterocarbon group. For example, comparative compound 1 contains a core of cyclohexane, which is similar to the cores of reactive modifiers 1-4. However, unlike reactive modifiers 1-4, comparative compound 1 contains only one silyl group. The results in Table 2 indicate that when comparative compound 1 is included in the moisture-curable resin composition, the cured products do not have any improvements in the mechanical properties over the control, Comparative Example 8. On the other hand, the results show that when reactive modifiers 1-4, each contains two or three silane groups, are included in the moisture-curable compositions, the cured products have significant improvements on tensile strength, modulus and hardness, with elongation around 100%. The same results can be observed when comparing the reactive modifiers 5 and 6 with the comparative compound 2.

Next, the relationship between mechanical properties of the cured products and the crosslinking density of the curable compositions is studied and the results are shown in Table 3. In table 3, the weight equivalent of the —Si(OCH$_3$)$_3$ group in the curable compositions are calculated to represent the crosslinking density of the resins obtained after cure.

The results show that an increase of crosslinking density may or may not affect the modulus of the cured resins. According to Table 3, comparative composition 2 has a relatively low crosslinking density. Upon cure, this composition exhibits no improvements at all in all mechanical properties. However, compositions of examples 17, 19, 20 and 21, each of which has a low crosslinking density similar to that of comparative composition 2, all exhibit improvements on tensile strength upon cure.

TABLE 3

Mechanical Properties of cured moisture-curable resin compositions at different equivalent weight percent of trimethoxysilyl groups

| Example | Reactive modifier component used in moisture-curable resin composition | Equivalent weight percent of —Si(OCH$_3$)$_3$ | Tensile Strength MPa (psi) | Young's Modulus (psi) | Elongation (%) | Hardness Shore A |
|---|---|---|---|---|---|---|
| Comp. 8 | Comparative 9 | 2 | 0.49 (71) | 0.40 (58) | 215 | 18 |
| Comp. 1 | Comparative 1 | 11 | 0.39 (57) | 0.45 (65) | 159 | 20 |
| Comp. 2 | Comparative 2 | 11.2 | 0.40 (58) | 0.39 (56) | 265 | 14 |
| Comp. 4 | Comparative 4 | 14.2 | 1.38 (200) | 2.44 (354) | 66 | 43 |

TABLE 3-continued

Mechanical Properties of cured moisture-curable resin compositions at different equivalent weight percent of trimethoxysilyl groups

| Example | Reactive modifier component used in moisture-curable resin composition | Equivalent weight percent of —Si(OCH$_3$)$_3$ | Tensile Strength MPa (psi) | Young's Modulus (psi) | Elongation (%) | Hardness Shore A |
|---|---|---|---|---|---|---|
| Comp. 5 | Comparative 3 | 16.6 | 1.61 (233) | 1.40 (203) | 137 | 42 |
| 12 | 1 | 16 | 5.52 (801) | 7.44 (1078) | 98 | 62 |
| 13 | 2 | 14 | 4.26 (618) | 3.84 (557) | 155 | 50 |
| 14 | 3 | 14 | 4.95 (718) | 5.11 (741) | 131 | 47 |
| 15 | 4 | 12.3 | 3.02 (438) | 4.54 (658) | 85 | 66 |
| 16 | 5 | 12 | 3.59 (520) | 3.42 (496) | 136 | 40 |
| 17 | 6 | 10.6 | 2.81 (407) | 2.14 (311) | 153 | 41 |
| 18 | 7 | 12.6 | 3.16 (459) | 4.16 (603) | 97 | 58 |
| 19 | 8 | 11.7 | 2.88 (417) | 3.14 (456) | 113 | 35 |
| 20 | 9 | 11 | 3.61 (524) | 4.37 (634) | 96 | 47 |
| 21 | 10 | 11 | 2.72 (395) | 2.04 (296) | 177 | 41 |

Example 22

Preparation of Moisture Curable Resin Composition, Curing and Mechanical Properties of Cured Composition Into Speed Mixer DAC 400 were charged with 1-(trimethoxy-silanyl)-3-[3-(trimethoxy-silanyl)-propyldisulfanyl]-propane, (25 grams, obtained from Momentive Performance Materials under the trade name Silquest™ A-1589 silane), trimethoxysilyl-terminated polyurethane polymer, moisture curable polymer (a) from example 11 (75 grams), dibutyltin dioxide (1 gram, obtained from Momentive Performance Materials, Inc. under the trade name Fomrez™ 11A) and bis(2-dimethylaminoethyl)ether (0.5 gram, obtained from Momentive Performance Materials, Inc. under the trade name Niax™ catalyst A-501). The mixture was stirred for 30 seconds at 17,000 rpm to provide a clear liquid. A film was drawn and cured in a humidity chamber at 50% relative humidity and 25° C. for 10 days. The cured film was tested according to ASTM C 661 and D 412. The cured film had a tensile strength at break of 4.94 MPa (717 psi), Young's modulus of 5.03 MPa (731 psi), % elongation at break of 140 and a Shore A hardness of 48.

Examples 23-34 and Comparative Examples 10-20

A series of compositions were prepared by blending the trimethoxysilyl-terminated polyurethane polymer, moisture curable polymer (a) from example 11, tin catalyst (Fomrex™ UL 11A from Momentive Performance Materials, Inc.) and one of the reactive modifier components 11 or 12 and comparative components 5 to 8 at various amounts of the reactive additive. The amount of the reactive additive (b) is expressed in weight percent based upon the total weight of components (a), (b) and (c). The amounts of reactive additive used in the composition are given in Table 4. Each mixture was stirred using a Speed Mixer DAC 400 for 30 second at 17,000 revolutions per minute (rpm). The mixture was a clear liquid having low viscosity. The mixture was then cast into a film and cured in a humidity chamber at 50% relative humidity and 25° C. for 10 days.

After cure, the mechanical properties of the moisture-curable resin compositions containing trimethoxysilyl-terminated polyurethane polymer (a) from example 11, Fomrex™ UL 11A catalyst (c) and one of the reactive modifier (b), components 11 to 13 and comparative components 5 to 8, were tested according to ASTM C 661 and D 412. All the results are listed in Table 4.

TABLE 4

Mechanical Properties of cured moisture-curable resin compositions at different reactive modifier concentrations

| Example | Reactive modifier | Reactive modifier wt. % | Crosslink Density Si/100 g. | Tensile Strength MPa (Psi) | Young's Modulus (psi) | Elongation % | Hardness Shore A |
|---|---|---|---|---|---|---|---|
| 23 | 11 | 10 | 0.361 | 1.10 (159) | 0.98 (142) | 178 | 31 |
| 24 | 11 | 20 | 0.722 | 2.07 (300) | 1.11 (161) | 238 | 34 |
| 25 | 11 | 30 | 1.083 | 4.04 (586) | 2.73 (396) | 200 | 41 |
| 26 | 11 | 40 | 1.444 | 6.81 (988) | 6.93 (1005) | 175 | 52 |
| 27 | 12 | 10 | 0.267 | 1.01 (147) | 0.94 (137) | 168 | 29 |
| 28 | 12 | 20 | 0.533 | 1.60 (232) | 1.54 (224) | 185 | 41 |
| 29 | 12 | 30 | 0.800 | 2.36 (342) | 4.23 (613) | 117 | 35 |
| 30 | 12 | 40 | 1.067 | unstable | unstable | unstable | unstable |
| 31 | 13 | 10 | 0.485 | 0.97 (140) | 0.94 (136) | 145 | 31 |
| 32 | 13 | 20 | 0.971 | 1.24 (180) | 0.97 (140) | 205 | 29 |
| 33 | 13 | 30 | 1.456 | 1.73 (251) | 1.05 (152) | 215 | 28 |
| 34 | 13 | 40 | 1.942 | 3.97 (576) | 2.96 (430) | 201 | 41 |
| Comp. 10 | Comp. 5 | 10 | 0.735 | 0.74 (107) | 1.24 (180) | 85 | 34 |
| Camp. 11 | Comp. 5 | 20 | 1.471 | 0.99 (144) | 1.54 (224) | 89 | 38 |
| Comp. 12 | Camp. 5 | 30 | 2.206 | 2.28 (330) | 1.83 (265) | 165 | 36 |
| Comp. 13 | Comp. 5 | 40 | 2.941 | 3.28 (475) | 3.59 (521) | 121 | 54 |
| Comp. 14 | Comp. 6 | 20 | 1.124 | 0.97 (140) | 0.73 (106) | 260 | 21 |

TABLE 4-continued

Mechanical Properties of cured moisture-curable resin compositions at different reactive modifier concentrations

| Example | Reactive modifier | Reactive modifier wt. % | Crosslink Density Si/100 g. | Tensile Strength MPa (Psi) | Young's Modulus (psi) | Elongation % | Hardness Shore A |
|---|---|---|---|---|---|---|---|
| Comp. 15 | Comp. 6 | 30 | 1.685 | 2.31 (335) | 0.84 (122) | 401 | 21 |
| Comp. 16 | Comp. 7 | 20 | 0.909 | 0.85 (123) | 0.70 (102) | 236 | 22 |
| Comp. 17 | Comp. 7 | 30 | 1.364 | 0.83 (120) | 0.84 (122) | 190 | 25 |
| Comp. 18 | Comp. 7 | 40 | 1.818 | 1.05 (152) | 0.70 (102) | 271 | 22 |
| Comp. 19 | Comp. 8 | 10 | 0.427 | (0.5) 73 | 0.46 (67) | 205 | 14 |
| Comp. 20 | Comp. 8 | 20 | 0.855 | Not cured | Not cured | Not cured | Not cured |

The results shown in Table 4 illustrate the benefit of using high loading of the reactive additive (b). The Young's modulus for the moisture-curable resin composition of Example 26, which contained 40 weight percent of the reactive additive 11, was six times larger than the modulus of the moisture curable resin composition of Comparative Example 2, which contained 10 weight percent of additive Comp. 8, while maintaining equivalent % elongation.

Example 35

Preparation of Moisture Curable Resin Composition, Curing and Mechanical Properties of the Cured Composition Before and after Aging at 120° C. for 3 Days A moisture curable resin composition was prepared according to Example 22. The composition was cured and the mechanical properties were tested according to ASTM C 661 and D 412. The samples of cured resin composition were then subjected to heating in an oven at 120° C. for 3 days and the mechanical properties were determined. The cured films were tested according to ASTM C 661 and D 412. The mechanical properties of the cured resin composition before and after aging at 120° C. for 3 days are given in Table 5.

Example 36

Preparation of Moisture Curable Resin Composition, Curing and Mechanical Properties of the Cured Composition Before and after Aging at 120° C. for 3 Days Into Speed Mixer DAC 400 were charged with triethoxy-octyl-silane (28.5 grams, obtained from Momentive Performance Materials under the trade name Silquest™ A-137 silane), vinyltrimethoxysilane (1.5 gram, obtained from Momentive Performance Materials under the trade name Silquest™ A-171 silane), trimethoxysilyl-terminated polyurethane polymer, moisture curable polymer (a) from example 11 (70 grams), dibutyltin dioxide (1 gram, obtained from Momentive Performance Materials, Inc. under the trade name Fomrez™ 11A) and bis(2-dimethylaminoethyl) ether (0.5 gram, obtained from Momentive Performance Materials, Inc. under the trade name Niax™ catalyst A-501). The mixture was stirred for 30 seconds at 17,000 rpm to provide a clear liquid. A film was drawn and cured in a humidity chamber at 50% relative humidity and 25° C. for 10 days. The mechanical properties cured film was tested according to ASTM C 661 and D 412. The samples of cured resin composition were then subjected to heating in an oven at 120° C. for 3 days and the mechanical properties were determined. The cured films were tested according to ASTM C 661 and D 412. The mechanical properties of the cured resin composition before and after aging at 120° C. for 3 days are given in Table 5.

Comparative Example 21

Preparation of Moisture Curable Resin Composition, Curing and Mechanical Properties of the Cured Composition Before and after Aging at 120° C. for 3 Days Into Speed Mixer DAC 400 were charged with trimethoxysilyl-terminated polyurethane polymer, moisture curable polymer (a) from example 11 (100 grams), and dibutyltin dioxide (1 gram, obtained from Momentive Performance Materials, Inc. under the trade name Fomrez™ 11A). The mixture was stirred for 30 seconds at 17,000 rpm to provide a clear liquid. A film was drawn and cured in a humidity chamber at 50% relative humidity and 25° C. for 7 days. The mechanical properties cured film was tested according to ASTM C 661 and D 412. The samples of cured resin composition were then subjected to heating in an oven at 120° C. for 3 days and the mechanical properties were determined. The cured film was tested according to ASTM C 661 and D 412. The mechanical properties of the cured resin composition before and after aging at 120° C. for 3 days are given in Table 5.

TABLE 5

Heat resistance of moisture curable polymers (a) containing different reactive modifiers (b)

| | Test condition | Tensile Strength @ break MPa (psi) | Elongation at break(%) | Young's Modulus MPa (psi) | Modulus @ 100% ext. MPa (psi) | Hardness Shore A |
|---|---|---|---|---|---|---|
| Example 35 | Initial | 4.94 (717) | 140 | 5.04 (731) | 3.08 (447) | 48 |
| | 120° C. for 3 days | 5.38 (780) | 125 | 6.10 (885) | 3.94 (571) | 58 |

TABLE 5-continued

Heat resistance of moisture curable polymers (a) containing different reactive modifiers (b)

|  | Test condition | Tensile Strength @ break MPa (psi) | Elongation at break(%) | Young's Modulus MPa (psi) | Modulus @ 100% ext. MPa (psi) | Hardness Shore A |
|---|---|---|---|---|---|---|
| Example 36 | Initial | 3.90 (565) | 200 | 3.14 (455) | 1.38 (200) | 35 |
|  | 120° C. for 3 days | 3.34 (485) | 190 | 2.83 (410) | 1.08 (156) | 33 |
| Comparative 21 | Initial | 0.5 (72) | 100 |  |  | 30 |
|  | 120° C. for 3 days | 0.01 (1) | 177 |  |  | 9 |

As shown in Table 5, the cured compositions of the present invention prepared from examples 35 and 36 had improved heat resistance after aging at 120° C. for 3 days compared to conventional resin composition prepared from comparative example 21. Without any additional thermal stabilizers, the mechanical properties of the cured resin composition of example 35 remained essentially the same after the 120° C. heat treatment. Although the cured resin composition of example 36 showed moderate reduction after the 120° C. heat treatment, the reduction in mechanical properties were much less that of the conventional resin composition of comparative example 21.

Examples 37

Primer Composition and its Properties

Into a mixing vessel were charged trimethoxysilyl-terminated polyurethane polymer, moisture curable polymer (a) from example 11 (80 grams), tin catalyst (0.8 grams of Fomrex™ UL 11A from Momentive Performance Materials, Inc.) and triethoxy-octyl-silane (20 grams of Silquest™ A-137 from Momentive Performance Materials). The mixture was stirred using a Speed Mixer DAC 400 for approximately 1 minute at 17,000 revolutions per minute (rpm). The mixture (33 grams) was diluted with glycidoxypropylt-rimethoxysilane (22 grams of Silquest™ A-187 silane from Momentive Performance Materials, Inc.), trimethoxy-methyl-silane (44 grams of Silquest™ A-1630 silane from Momentive Performance Materials, Inc.), and polyalkylene-oxide modified polymethylsiloxane (1 gram of Silwet™ L-7500 from Momentive Performance Materials, Inc.), toluene (850 grams) and n-heptane (50 grams). The primer was brushed onto a thermoplastic olefin membrane used in roofing applications, dried overnight. Then a bead of low modulus construction sealant based upon a silylated polyurethane polymer (SPUR™ 1015 from Momentive Performance Materials, Inc.) was applied on top of the primer layer, and cured in a humidity chamber at 50% relative humidity and 25° C. for 7 days. The peel strength using a test specimen with a linear inch width (2.54 cm) and mode of failure were determined and are reported in Table 6.

Examples 38

Primer Composition and its Properties

Into a mixing vessel were charged trimethoxysilyl-terminated polyurethane polymer, moisture curable polymer (a) from example 11 (80 grams) tin catalyst (0.8 grams of Fomrex™ UL 11A from Momentive Performance Materials, Inc.) and triethoxy-octyl-silane (20 grams of Silquest™ A-137 from Momentive Performance Materials). The mixture was stirred using a Speed Mixer DAC 400 for approximately 1 minute at 17,000 revolutions per minute (rpm). The mixture (33 grams) was diluted with glycidoxypropylt-rimethoxysilane (22 grams of Silquest™ A-187 silane from Momentive Performance Materials, Inc.), trimethoxy-methyl-silane (44 grams of Silquest™ A-1630 silane from Momentive Performance Materials, Inc.), and polyalkylene-oxide modified polymethylsiloxane (1 gram of Silwet™ L-7500 from Momentive Performance Materials, Inc.), isod-odecane (740 grams) and acetone (160 grams). The primer was brushed onto a thermoplastic olefin membrane used in roofing applications, dried overnight. Then a bead of low modulus construction sealant based upon a silylated polyurethane polymer (SPUR™ 1015 from Momentive Performance Materials, Inc.) was applied on top of the primer layer and cured in a humidity chamber at 50% relative humidity and 25° C. for 7 days. The peel strength using a test specimen with a linear inch width (2.54 cm) and mode of failure were determined and are reported in Table 6.

Comparative Examples 22

TPO Primer and its Properties

A TPO Primer from Chem Link, Inc. was brushed onto a thermoplastic olefin membrane used in roofing applications, dried overnight and then a bead of low modulus construction sealant based upon a silylated polyurethane polymer (SPUR™ 1015 from Momentive Performance Materials, Inc.) was applied and cured in a humidity chamber at 50% relative humidity and 25° C. for 7 days. The peel strength using a test specimen with a linear inch width (2.54 cm) and mode of failure were determined and are reported in Table 6.

TABLE 6

Peel strength and mode of failure from primed thermoplastic olefin membranes

| Example | Example 37 | Example 38 | Comparative Example 22 |
|---|---|---|---|
| Peel strength MPa (psi) | 0.12 (17.3) | 0.17 (24) | 0.14 (21) |
| Failure mode, % | 100% cohesive | 100% cohesive | 100% cohesive |

Example 39

Hot Melt Adhesive Composition of the Invention

A thermoplastic polymer (42 grams of Escorene™ Polyvinylacetate UL 7710 from ExxonMobil Chemical Company, having a melt index of 420 grams per 10 minutes, a density of 0.941 g/cm³, a vinyl acetate content of 26.7 weight percent and a tensile at break of 232 psi), an aromatic tackifying agent (41.8 grams of Escorez™ 2394, an aromatic modified aliphatic resin from ExxonMobil Chemical Company, having a softening point of 9° C.), an aliphatic tackifying agent (4.5 grams of Escorez™ 1304, an aliphatic hydrocarbon resin from ExxonMobil Chemical Company, having softening point of 100° C.) and free radical stabilizer (0.4 gram of Irganox 1010 from Ciba Specialty Chemicals) were mixed in a mixing bowl roller blade mixer for 15-30 minutes at a temperature of 170° C. at a rotor speed of 120 revolutions per minute (rpm). The mixing bowl was connected to a Brabender Plasticorder. When well blended, trimethoxysilyl-terminated polyurethane polymer, moisture curable polymer (a) from example 11 (8.0 grams) was added and mixed for 15-30 minutes. Trimethoxy-vinyl-silane (1.65 gram of Silquest™ A-171 from Momentive Performance Materials, Inc.) and free radical-generating agent (0.15 grams of Triganox™ 42S from AkzoNobel Corporation) were then added and mixed for 15-30 minutes at 170° C. and rotor speed of 120 rpm. The physical properties of the hot melt adhesive and its adhesion to bare aluminum substrate are given in Table 7.

Comparative Example 23

Comparative Hot Melt Adhesive Composition

A thermoplastic polymer (42 grams of Escorene™ Polyvinylacetate UL 7710 from ExxonMobil Chemical Company, having a melt index of 420 grams per 10 minutes, a density of 0.941 g/cm³, a vinyl acetate content of 26.7 weight percent and a tensile at break of 232 psi), an aromatic tackifying agent (43.3 grams of Escorez™ 2394, an aromatic modified aliphatic resin from ExxonMobil Chemical Company, having a softening point of 9° C.), an aliphatic tackifying agent (4.5 grams of Escorez™ 1304, an aliphatic hydrocarbon resin from ExxonMobil Chemical Company, having softening point of 100° C.) and free radical stabilizer (0.4 gram of Irganox™ 1010 from Ciba Specialty Chemicals) were mixed in a mixing bowl roller blade mixer for 15-30 minutes at a temperature of 170° C. at a rotor speed of 120 revolutions per minute (rpm). The mixing bowl was connected to a Brabender Plasticorder. When well blended, trimethoxysilyl-terminated polyurethane polymer, moisture curable polymer (a) from example 11 (8.0 grams) and triethoxy-octyl-silane (1.5 gram of Silquest™ A-137 from Momentive Performance Materials, Inc) were added and mixed for 15-30 minutes. Trimethoxy-vinyl-silane (1.65 gram of Silquest™ A-171 from Momentive Performance Materials, Inc.) and free radical-generating agent (0.15 grams of Triganox™ 42S from AkzoNobel Corporation) were then added and mixed for 15-30 minutes at 170° C. and rotor speed of 120 rpm. The physical properties of the hot melt adhesive and its adhesion to bare aluminum substrate are given in Table 7.

TABLE 7

The physical properties and adhesion to bare aluminum of hot melt adhesives

| Example No. | Example 39 | Comparative Example 23 |
|---|---|---|
| Maximum load, MPa (psi) | 0.89 (129) | 0.79 (115) |
| Strain at maximum load, % | 9 | 12 |
| Failure mode | cohesive | cohesive |

The addition of triethoxy-octyl-silane to the formulation resulted in a 13 percent increase in the maximum load.

It will be understood that other than in the working examples or where otherwise indicated, all numbers expressing amounts of materials, and so forth, stated in the specification and claims are to understood as being modified in all instances by the term "about".

It will be understood that any numerical range recited herein includes all sub-ranges with that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

What is claimed is:

1. A moisture-curable resin composition comprising:
   (a) a moisture-curable polymer having at least one hydrolysable silyl group having the general Formula (3):

$$R^6\text{—}[O\text{—}R^7\text{—}Si(X^1X^2X^3)]_f \quad (3)$$

wherein:
   each occurrence of $R^6$ is independently a monovalent or polyvalent organic polymer fragment having a number average molecular weight of from 500 to 25,000 grams per mole and derived from polyols selected from the group consisting of hydroxyl-terminated polyalkylene oxides diol, hydroxyl-terminated polyalkylene oxides triol, polycaprolactone diol, polycaprolactone triol, hydroxyl terminated unsaturated rubber, and polyester made from saturated aliphatic, unsaturated and/or aromatic diacids and diols and/or triols;
   each occurrence of $R^7$ is independently a divalent alkylene, alkenylene, arenylene, arylene or aralkylene group containing up to 12 carbon atoms;
   each occurrence of $X^1$ is independently $R^9O\text{—}$, wherein each $R^9$ is independently selected from the group consisting of hydrogen, alkyl, alkenyl, arenyl, aryl, and aralkyl groups, wherein each $R^9$, other than hydrogen, contains from 1 to 18 carbon atoms and, optionally, contains at least one oxygen or sulfur atom;
   each occurrence of $X^2$ and $X^3$ is independently selected from the group consisting of $R^9O\text{—}$ and $R^{10}$ wherein each $R^9$ is independently selected from the group consisting of hydrogen, alkyl, alkenyl, arenyl, aryl, and aralkyl, wherein each $R^9$, other than hydrogen, contains from 1 to 18 carbon atoms and, optionally, contains at least one oxygen or sulfur atom and each $R^{10}$ is independently an alkyl group containing from 1 to 6 carbon atoms; and
   f is an integer wherein f is 1 to 6; and
   (b) a reactive modifier having the general Formula (1):

$$G^1[\text{—}R^1SiR^2_a(OR^3)_{3-a}]_b \quad (\text{Formula 1})$$

wherein:
   $G^1$ is selected from the group consisting of a divalent and polyvalent monocyclic hydrocarbon group containing from 5 to 16 carbon atoms, a divalent and polyvalent cyclic heterocarbon group containing from 3 to 16 carbon atoms wherein the heteroatom are selected from the group consisting of oxygen, silicon and sulfur; and a divalent and polyvalent cyclic silicone group containing from 3 to 8 silicon atoms and from 3 to 8 oxygen atoms;

each occurrence of $R^1$ is independently selected from the group consisting of a covalent bond between the silicon atom and $G^1$, a divalent hydrocarbon group containing from 1 to 18 carbon atoms;

each occurrence of $R^2$ is monovalent hydrocarbon containing from 1 to 12 carbon atoms;

each occurrence of $R^3$ is monovalent hydrocarbon containing from 1 to 12 carbon atoms;

each occurrence of a and b is independently an integer, wherein a is 0 to 2; and b is 2 to 6, with the provisos that,
  (i) when $R^1$ is a chemical bond, then the silicon atom is covalently bonded to a carbon atom of $G^1$;
  (ii) when $R^1$ contains a heteroatom, the silicon atom is bonded to a carbon atom of $R^1$;
and (c) a catalyst for catalyzing the reaction between the moisture-curable polymer (a) and reactive modifier (b) under curing conditions selected from the group consisting of an organic dibutyltin, zirconium complex, aluminum chelate, titanic chelate, organic zinc, organic cobalt, organic iron, organic nickel, organobismuth, amine and mixtures of organometallic compounds and amine, and wherein component (a) is present in an amount of from 30 weight percent to 95 weight percent based upon the total weight of (a), (b) and (c); component (b) is present in an amount of from 5 weight percent to 70 weight percent based upon the total weight of (a), (b) and (c); and component (c) is present in an amount of from 0.05 weight percent to 5 weight percent based upon the total weight of (a), (b) and (c).

2. The moisture-curable composition of claim 1, wherein the catalyst (c) is an organic dibutyltin, aluminum chelate, organic zinc, organobismuth and amine.

3. The moisture-curable resin composition of claim 2, wherein the moisture-curable resin composition comprises from 50 weight percent to 90 weight percent based upon the total weight of components (a), (b) and (c) a moisture-curable polymer having at least one hydrolysable group (a), from 10 to 50 weight percent based upon the total weight of components (a), (b) and (c) a reactive modifier (b), and from 0.1 weight percent to 3 weight percent based upon the total weight of components (a), (b) and (c), a catalysts, wherein $G^1$ is a divalent or polyvalent cyclic hydrocarbon containing from 6 to 10 carbon atoms; each occurrence of $R^1$ and $R^7$ is independently an alkylene group of from 1 to 6 carbon atoms; each occurrence of $R^2$ and $R^3$, is independently an alkyl group of from 1 to 4 carbon atoms; a is 0 or 1; b is 2 or 3; and f is 2.

4. The moisture-curable resin composition of claim 3, wherein the moisture-curable resin composition comprises from 60 weight percent to 80 weight percent based upon the total weight of components (a), (b) and (c) a moisture-curable polymer having at least one hydrolysable group (a), from 20 to 40 weight percent based upon the total weight of components (a), (b) and (c) a reactive modifier (b), and from 0.5 weight percent to 2 weight percent based upon the total weight of components (a), (b) and (c), a catalysts, wherein $G^1$ is a divalent or polyvalent cyclic hydrocarbon derivable from cyclohexane, cyclooctane and cyclodecane; each occurrence of $R^1$ and $R^7$ is independently methylene, ethylene or propylene; each occurrence of $R^2$ and $R^3$, is independently methyl or ethyl; a is 0; b is 3; and f is 2.

5. The moisture-curable composition of claim 2, wherein the moisture-curable resin composition comprises 60 weight percent to 80 weight percent based upon the total weight of components (a), (b) and (c) a moisture-curable polymer having at least one hydrolysable group (a), from 20 to 40 weight percent based upon the total weight of components (a), (b) and (c) a reactive modifier (b), and from 0.5 weight percent to 2 weight percent based upon the total weight of components (a), (b) and (c), a catalysts, wherein $G^1$ is a divalent or polyvalent monocyclic hydrocarbon derivable from cyclohexane, cyclooctane and cyclodecane; each occurrence of $R^1$ and $R^7$ is independently methylene, ethylene or propylene; each occurrence of $R^2$, $R^3$, $R^9$ and $R^{10}$ is independently methyl or ethyl; a is 0 or 1; b is 2 or 3; and f is 2.

6. A cured moisture-curable resin composition made by curing the moisture-curable resin composition of claim 1.

7. The cured moisture-curable resin composition of claim 6, wherein the reactive modifier (b) is selected from the group consisting of 1,2,4-tris-[2-(trimethoxy-silanyl)-ethyl]-cyclohexane, 1,2,4-tris-[2-(dimethoxy-methyl-silanyl)-ethyl]-cyclohexane, 1,2,4-tris[2-(triethoxy-silanyl)-ethyl]-cyclohexane, 1,2,4-tris-[2-(tripropoxy-silanyl)-ethyl]-cyclohexane, 1,4-bis[2-(trimethoxy-silanyl)-ethyl]-2-vinyl-cyclohexane, 1,4-bis-[2-(dimethoxy-methyl-silanyl)-ethyl]-2-vinyl-cyclohexane, 1,4-bis-[2-(triethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl)-ethyl)-1,1,3,3-tetramethyl-disiloxane, 1-(2-{2,5-bis-[2-(dimethoxy-methyl-silanyl)-ethyl)-cyclohexyl]-ethyl)-3-(2-(2,4-bis-[2-(dimethoxy-methyl-silanyl)-ethyl]-cyclohexyl}-ethyl)-1,1,3,3-tetramethyl-disiloxane, 1-(2-{2,5-bis-[2-(triethoxy-silanyl)-ethyl]-cyclohexyl}-ethyl)-3-(2-(2,4-bis-[2-(triethoxy-silanyl)-ethyl]-cyclohexyl}-ethyl)-1,1,3,3-tetramethyl-disiloxane, 2,5-bis-[2-(trimethoxy-silanyl)-ethyl]-bicyclo[2.2.1]heptane, 2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(dimethoxy-methyl-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, and mixtures thereof.

8. A moisture-curable sealant, coating or adhesive made from the moisture-curable composition of claim 1.

9. A moisture-curable resin composition comprising:
  (a) a moisture-curable polymer having at least one hydrolysable silyl group having the general Formula (3):

$$R^6-[O-R^7-Si(X^1X^2X^3)]_f \qquad (3)$$

wherein:
  each occurrence of $R^6$ is independently a monovalent or polyvalent organic polymer fragment having a number average molecular weight of from 500 to 25,000 grams per mole and derived from polyols selected from the group consisting of hydroxyl-terminated polyalkylene oxides diol, hydroxyl-terminated polyalkylene oxides triol, polycaprolactone diol, polycaprolactone triol, hydroxyl terminated unsaturated rubber, and polyester made from saturated aliphatic, unsaturated and/or aromatic diacids and diols and/or triols;
  each occurrence of $R^7$ is independently a divalent alkylene, alkenylene, arenylene, arylene or aralkylene group containing up to 12 carbon atoms;
  each occurrence of $X^1$ is independently $R^9O-$, wherein each $R^9$ is independently selected from the group consisting of hydrogen, alkyl, alkenyl, arenyl, aryl, and aralkyl groups, wherein each $R^9$, other than hydrogen, contains from 1 to 18 carbon atoms and, optionally, contains at least one oxygen or sulfur atom;

each occurrence of $X^2$ and $X^3$ is independently selected from the group consisting of $R^9O$— and $R^{10}$ wherein each $R^9$ is independently selected from the group consisting of hydrogen, alkyl, alkenyl, arenyl, aryl, and aralkyl, wherein each $R^9$, other than hydrogen, contains from 1 to 18 carbon atoms and, optionally, contains at least one oxygen or sulfur atom and each $R^{10}$ is independently an alkyl group containing from 1 to 6 carbon atoms; and f is an integer wherein f is 1 to 6;

(b) a reactive modifier having the general Formula (1):

  (Formula 1)

wherein:

$G^1$ is selected from the group consisting of a divalent and polyvalent cyclic hydrocarbon group containing from 5 to 16 carbon atoms, a divalent and polyvalent cyclic heterocarbon group containing from 3 to 16 carbon atoms wherein the heteroatom are selected from the group consisting of oxygen, silicon and sulfur; and a divalent and polyvalent cyclic silicone group containing from 3 to 8 silicon atoms and from 3 to 8 oxygen atoms;

each occurrence of $R^1$ is independently selected from the group consisting of a covalent bond between the silicon atom and $G^1$, a divalent hydrocarbon group containing from 1 to 18 carbon atoms, and optionally at least one heteroatom selected from the group consisting of oxygen, silicon and sulfur;

each occurrence of $R^2$ is monovalent hydrocarbon containing from 1 to 12 carbon atoms;

each occurrence of $R^3$ is monovalent hydrocarbon containing from 1 to 12 carbon atoms;

each occurrence of a and b is independently an integer, wherein a is 0 to 2; and b is 2 to 6, with the provisos that, (i) when $R^1$ is a chemical bond, then the silicon atom is covalently bonded to a carbon atom of $G^1$;

(ii) when $R^1$ contains a heteroatom, the silicon atom is bonded to a carbon atom of $R^1$, wherein the reactive modifier (b) is selected from the group consisting of 1,2,4-tris-[2-(trimethoxy-silanyl)-ethyl]-cyclohexane, 1,2,4-tris-[2-(dimethoxy-methyl-silanyl)-ethyl]-cyclohexane, 1,2,4-tris[2-(triethoxy-silanyl)-ethyl]-cyclohexane, 1,2,4-tris-[2-(tripropoxy-silanyl)-ethyl]-cyclohexane, 1,4-bis[2-(trimethoxy-silanyl)-ethyl]-2-vinyl-cyclohexane, 1,4-bis-[2-(dimethoxy-methyl-silanyl)-ethyl]-2-vinyl-cyclohexane, 1,4-bis-[2-(triethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, 1-(2-{2,5-bis-[2-(dimethoxy-methyl-silanyl)-ethyl]-cyclohexyl}-ethyl)-3-(2-{2,4-bis-[2-(dimethoxy-methyl-silanyl)-ethyl]-cyclohexyl}-ethyl)-1,1,3,3-tetramethyl-disiloxane, 1-(2-{2,5-bis-[2-(triethoxy-silanyl)-ethyl]-cyclohexyl}-ethyl)-3-(2-{2,4-bis-[2-(triethoxy-silanyl)-ethyl]-cyclohexyl}-ethyl)-1,1,3,3-tetramethyl-disiloxane, 2,5-bis-[2-(trimethoxy-silanyl)-ethyl]-bicyclo[2.2.1]heptane, 2,5-bis[2-(dimethoxy-methyl-silanyl)-ethyl]-bicyclo[2.2.1]heptane, 2,5-bis-[2-(triethoxy-silanyl)-ethyl]-bicyclo[2.2.1]heptane, 1-(2-{6-[2-(trimethoxy-silanyl)-ethyl]-bicyclo[2.2.1]hept-2-yl}-ethyl)-3-(2-{5-[2-(trimethoxy-silanyl)-ethyl]-bicyclo[2.2.1]hept-2-yl}-ethyl)-1,1,3,3-tetramethyl-disiloxane, 1-(2-{6-[2-(dimethoxy-methyl-silanyl)-ethyl]-bicyclo[2.2.1]hept-2-yl}-ethyl)-3-(2-{5-[2-(dimethoxy-methyl-silanyl)-ethyl]-bicyclo[2.2.1]hept-2-yl}-ethyl)-1,1,3,3-tetramethyl-disiloxane, 1-(2-{6-[2-(triethoxy-silanyl)-ethyl]-bicyclo[2.2.1]hept-2-yl}-ethyl)-3-(2-{5-[2-(triethoxy-silanyl)-ethyl]-bicyclo[2.2.1]hept-2-yl}-ethyl)-1,1,3,3-tetramethyl-disiloxane, 1,4-bis[2-(trimethoxy-silanyl)-ethyl]-benzene, 1,4-bis-[2-(dimethoxy-methyl-silanyl)-ethyl]-benzene, 1,4-bis-[2-(triethoxy-silanyl)-ethyl]-benzene, 2,4,6,8-tetrakis-[2-(trimethoxy-silanyl)-ethyl]-2,4,6,8-tetramethyl-[1,3,5,7,2,4,6,8]tetroxatetrasilocane, 2,4,6,8-tetrakis-[2-(dimethoxy-methyl-silanyl)-ethyl]-2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(dimethoxy-methyl-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, and mixtures thereof; and (c) a catalyst for catalyzing the reaction between the moisture-curable polymer (a) and reactive modifier (b) under curing conditions selected from the group consisting of an organic dibutyltin, zirconium complex, aluminum chelate, titanic chelate, organic zinc, organic cobalt, organic iron, organic nickel, organobismuth, amine and mixtures of organometallic compounds and amine, and wherein component (a) is present in an amount of from 30 weight percent to 95 weight percent based upon the total weight of (a), (b) and (c); component (b) is present in an amount of from 5 weight percent to 70 weight percent based upon the total weight of (a), (b) and (c); and component (c) is present in an amount of from 0.05 weight percent to 5 weight percent based upon the total weight of (a), (b) and (c).

10. The moisture-curable resin composition of claim 9, wherein the reactive modifier (b) is selected from the group consisting of 1,2,4-tris-[2-(triethoxy-silanyl)-ethyl]-cyclohexane, and 2,4,6,8-tetrakis-[2-(triethoxy-silanyl)-ethyl]-2,4,6,8-tetramethyl-[1,3,5,7,2,4,6,8]tetroxatetrasilocane.

11. A moisture-curable resin composition comprising:

(a) a moisture-curable polymer having at least one hydrolysable silyl group having the general Formula (3):

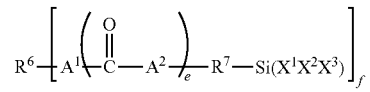

wherein:

each occurrence of $R^6$ is independently a monovalent or polyvalent organic polymer fragment having a number average molecular weight of from 500 to 25,000 grams per mole and derived from polyols selected from the group consisting of hydroxyl-terminated polyalkylene oxides diol, hydroxyl-terminated polyalkylene oxides triol, polycaprolactone diol, polycaprolactone triol, hydroxyl terminated unsaturated rubber, and polyester made from saturated aliphatic, unsaturated and/or aromatic diacids and diols and/or triols;

each occurrence of $R^7$ is independently a divalent alkylene, alkenylene, arenylene, arylene or aralkylene group containing up to 12 carbon atoms;

each occurrence of $A^1$ is independently selected from divalent oxygen atom, sulfur atom, or substituted nitrogen of the structure (—)$_2$NR$^8$, wherein R$^8$ is hydrogen, alkyl, alkenyl, arenyl, aryl, aralkyl or —R$^7$SiX$^1$X$^2$X$^3$ group, wherein each R$^8$, other than hydrogen, contains from 1 to 18 carbon atoms, and with the provisos that when $A^1$ is oxygen or sulfur, then $A^2$ is (—)$_2$NR$^8$;

each occurrence of $A^2$ is independently selected from divalent oxygen atom, sulfur atom or substituted nitrogen of the structure (—)$_2$NR$^8$, —NR$^8$(C═O)NR$^8$—, —NR$^8$(C═O)O—, and —NR$^8$(C═O)S—, wherein R$^8$ is hydrogen, alkyl, alkenyl, arenyl, aryl, aralkyl or —R$^7$SiX$^1$X$^2$X$^3$ group, wherein each R$^8$, other than hydrogen, contains from 1 to 18 carbon atoms, and with the provisos that when $A^2$ is oxygen or sulfur, then $A^1$ is (—)$_2$NR$^8$;

each occurrence of $X^1$ is independently R$^9$O—, wherein each R$^9$ is independently selected from the group consisting of hydrogen, alkyl, alkenyl, arenyl, aryl, and aralkyl groups, wherein each R$^9$, other than hydrogen, contains from 1 to 18 carbon atoms and, optionally, contains at least one oxygen or sulfur atom;

each occurrence of $X^2$ and $X^3$ is independently selected from the group consisting of R$^9$O— and R$^{10}$ wherein each R$^9$ is independently selected from the group consisting of hydrogen, alkyl, alkenyl, arenyl, aryl, and aralkyl, wherein each R$^9$, other than hydrogen, contains from 1 to 18 carbon atoms and, optionally, contains at least one oxygen or sulfur atom and each R$^{10}$ is independently an alkyl group containing from 1 to 6 carbon atoms; and each occurrence of subscripts e and f is independently an integer wherein e is 1 and f is 1 to 6;

(b) a reactive modifier having the general Formula (1):

$$G^1[-R^1SiR^2_a(OR^3)_{3-a}]_b \quad \text{(Formula 1)}$$

wherein:
$G^1$ is selected from the group consisting of a divalent and polyvalent cyclic hydrocarbon group containing from 5 to 16 carbon atoms, a divalent and polyvalent cyclic heterocarbon group containing from 3 to 16 carbon atoms wherein the heteroatom are selected from the group consisting of oxygen, silicon and sulfur; and a divalent and polyvalent cyclic silicone group containing from 3 to 8 silicon atoms and from 3 to 8 oxygen atoms;

each occurrence of R$^1$ is independently selected from the group consisting of a covalent bond between the silicon atom and G$^1$, a divalent hydrocarbon group containing from 1 to 18 carbon atoms, and optionally at least one heteroatom selected from the group consisting of oxygen, silicon and sulfur;

each occurrence of R$^2$ is monovalent hydrocarbon containing from 1 to 12 carbon atoms;

each occurrence of R$^3$ is monovalent hydrocarbon containing from 1 to 12 carbon atoms;

each occurrence of a and b is independently an integer, wherein a is 0 to 2; b is 2 to 6, with the provisos that, (i) when R$^1$ is a chemical bond, then the silicon atom is covalently bonded to a carbon atom of d; (ii) when R$^1$ contains a heteroatom, the silicon atom is bonded to a carbon atom of R$^1$; and (c) a catalyst for catalyzing the reaction between the moisture-curable polymer (a) and reactive modifier (b) under curing conditions selected from the group consisting of an organic dibutyltin, zirconium complex, aluminum chelate, titanic chelate, organic zinc, organic cobalt, organic iron, organic nickel, organobismuth, amine and mixtures of organometallic compounds and amine; and wherein component (a) is present in an amount of from 30 weight percent to 95 weight percent based upon the total weight of (a), (b) and (c); component (b) is present in an amount of from 5 weight percent to 70 weight percent based upon the total weight of (a), (b) and (c); and component (c) is present in an amount of from 0.05 weight percent to 5 weight percent based upon the total weight of (a), (b) and (c).

12. The moisture-curable resin composition of claim 11, wherein the moisture-curable resin composition comprises from 60 weight percent to 80 weight percent based upon the total weight of components (a), (b) and (c) a moisture-curable polymer having at least one hydrolysable group (a), from 20 to 40 weight percent based upon the total weight of components (a), (b) and (c) a reactive modifier (b), and from 0.5 weight percent to 2 weight percent based upon the total weight of components (a), (b) and (c), a catalysts, wherein G$^1$ is a divalent or polyvalent cyclic hydrocarbon derivable from cyclohexane, cyclooctane and cyclodecane; each occurrence of R$^1$ and R$^7$ is independently methylene, ethylene or propylene; each occurrence of R$^2$ and R$^3$ is independently methyl or ethyl; R$^8$ is hydrogen; each occurrence of A$^1$ is independently oxygen (—O—) or —NR$^8$—; each occurrence of A$^2$ is independently oxygen (—O—) or —NR$^8$—; a is 0; b is 3; and f is 2.

13. The moisture-curable resin composition of claim 11, wherein the reactive modifier (b) is selected from the group consisting of 1,2,4-tris-[2-(trimethoxy-silanyl)-ethyl]-cyclohexane, 1,2,4-tris[2-(dimethoxy-methyl-silanyl)-ethyl]-cyclohexane, 1,2,4-tris-[2-(triethoxy-silanyl)-ethyl]-cyclohexane, 1,2,4-tris-[2-(tripropoxy-silanyl)-ethyl]-cyclohexane, 1,4-bis[2-(trimethoxy-silanyl)-ethyl]-2-vinyl-cyclohexane, 1,4-bis-[2-(dimethoxy-methyl-silanyl)-ethyl]-2-vinyl-cyclohexane, 1,4-bis-[2-(triethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, 1-(2-{2,5-bis-[2-(dimethoxy-methyl-silanyl)-ethyl]-cyclohexyl}-ethyl)-3-(2-{2,4-bis-[2-(dimethoxy-methyl-silanyl)-ethyl]-cyclohexyl}-ethyl)-1,1,3,3-tetramethyl-disiloxane, 1-(2-{2,5-bis-[2-(triethoxy-silanyl)-ethyl]-cyclohexyl}-ethyl)-3-(2-{2,4-bis-[2-(triethoxy-silanyl)-ethyl]-cyclohexyl}-ethyl)-1,1,3,3-tetramethyl-disiloxane, 2,5-bis-[2-(trimethoxy-silanyl)-ethyl]bicyclo[2.2.1]heptane, 2,5-bis-[2-(dimethoxy-methyl-silanyl)-ethyl]-bicyclo[2.2.1]heptane, 2,5-bis-[2-(triethoxy-silanyl)-ethyl]-bicyclo[2.2.1]heptane, 1-(2-{6-[2-(trimethoxy-silanyl)-ethyl]-bicyclo[2.2.1]hept-2-yl}-ethyl)-3-(2-{5-[2-(trimethoxy-silanyl)-ethyl]-bicyclo[2.2.1]hept-2-yl}-ethyl)-1,1,3,3-tetramethyl-disiloxane, 1-(2-{6-[2-(dimethoxy-methyl-silanyl)-ethyl]-bicyclo[2.2.1]hept-2-yl}-ethyl)-3-(2-{5-[2-(dimethoxy-methyl-silanyl)-ethyl]-bicyclo[2.2.1]hept-2-yl}-ethyl)-1,1,3,3-tetramethyl-disiloxane, 1-(2-{6-[2-(triethoxy-silanyl)-ethyl]-bicyclo[2.2.1]hept-2-yl}-ethyl)-3-(2-{5-[2-(triethoxy-silanyl)-ethyl]-bicyclo[2.2.1]hept-2-yl}-ethyl)-1,1,3,3-tetramethyl-disiloxane, 1,4-bis-[2-(trimethoxy-silanyl)-ethyl]-benzene, 1,4-bis[2-(dimethoxy-methyl-silanyl)-ethyl]-benzene, 1,4-bis[2-(triethoxy-silanyl)-ethyl]-benzene, 2,4,6,8-tetrakis-[2-(trimethoxy-silanyl)-ethyl]-2,4,6,8-tetramethyl-[1,3,5,7,2,4,6,8]tetroxatetrasilocane, 2,4,6,8-tetrakis-[2-(dimethoxy-methyl-silanyl)-ethyl]-2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]

tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(dimethoxy-methyl-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, and mixtures thereof.

14. A cured moisture-curable resin composition made by curing the moisture curable resin composition of claim 11.

15. The cured moisture-curable resin composition of claim 14, wherein the reactive modifier (b) is selected from the group consisting of 1,2,4-tris-[2-(trimethoxy-silanyl)-ethyl]-cyclohexane, 1,2,4-tris-[2-(dimethoxy-methyl-silanyl)-ethyl]-cyclohexane, 1,2,4-tris[2-(triethoxy-silanyl)-ethyl]-cyclohexane, 1,2,4-tris-[2-(tripropoxy-silanyl)-ethyl]-cyclohexane, 1,4-bis[2-(trimethoxy-silanyl)-ethyl]-2-vinyl-cyclohexane, 1,4-bis-[2-(dimethoxy-methyl-silanyl)-ethyl]-2-vinyl-cyclohexane, 1,4-bis-[2-(triethoxy-silanyl)-ethyl]-2-vinyl-cyclohexane, 1-(2-{2,5-bis-[2-(trimethoxy-silanyl)-ethyl]-cyclohexyl}-ethyl)-3-(2-{2,4-bis-[2-(trimethoxy-silanyl)-ethyl]-cyclohexyl}-ethyl)-1,1,3,3-tetramethyl-disiloxane, 1-(2-{2,5-bis-[2-(dimethoxy-methyl-silanyl)-ethyl]-cyclohexyl}-ethyl)-3-(2-{2,4-bis-[2-(dimethoxy-methyl-silanyl)-ethyl]-cyclohexyl}-ethyl)-1,1,3,3-tetramethyl-disiloxane, 1-(2-{2,5-bis-[2-(triethoxy-silanyl)-ethyl]-cyclohexyl}-ethyl)-3-(2-{2,4-bis-[2-(triethoxy-silanyl)-ethyl]-cyclohexyl}-ethyl)-1,1,3,3-tetramethyl-disiloxane, 2,5-bis-[2-(trimethoxy-silanyl)-ethyl]-bicyclo[2.2.1]heptane, 2,5-bis[2-(dimethoxy-methyl-silanyl)-ethyl]-bicyclo[2.2.1]heptane, 2,5-bis-[2-(triethoxy-silanyl)-ethyl]-bicyclo[2.2.1]heptane, 1-(2-{6-[2-(trimethoxy-silanyl)-ethyl]-bicyclo[2.2.1]hept-2-yl}-ethyl)-3-(2-{5-[2-(trimethoxy-silanyl)-ethyl]bicyclo[2.2.1]hept-2-yl}-ethyl)-1,1,3,3-tetramethyl-disiloxane, 1-(2-{6-[2-(dimethoxy-methyl-silanyl)-ethyl]-bicyclo[2.2.1]hept-2-yl}-ethyl)-3-(2-{5-[2-(dimethoxy-methyl-silanyl)-ethyl]-bicyclo[2.2.1]hept-2-yl}-ethyl)-1,1,3,3-tetramethyl-disiloxane, 1-(2-{6-[2-(triethoxy-silanyl)-ethyl]-bicyclo[2.2.1]hept-2-yl}-ethyl)-3-(2-{5-[2-(triethoxy-silanyl)-ethyl]-bicyclo[2.2.1]hept-2-yl}-ethyl)-1,1,3,3-tetramethyl-disiloxane, 1,4-bis[2-(trimethoxy-silanyl)-ethyl]-benzene, 1,4-bis-[2-(dimethoxy-methyl-silanyl)-ethyl]-benzene, 1,4-bis[2-(triethoxy-silanyl)-ethyl]-benzene, 2,4,6,8-tetrakis-[2-(trimethoxy-silanyl)-ethyl]-2,4,6,8-tetramethyl-[1,3,5,7,2,4,6,8]tetroxatetrasilocane, 2,4,6,8-tetrakis-[2-(dimethoxy-methyl-silanyl)-ethyl]-2,4,6,8-tetramethyl-[1,3,5,7,2,4,6,8]tetroxatetrasilocane, 2,4,6,8-tetrakis-[2-(triethoxy-silanyl)-ethyl]-2,4,6,8-tetramethyl-[1,3,5,7,2,4,6,8]tetroxatetrasilocane, 2,4,6-tris-[2-(trimethoxy-silanyl)-ethyl]-2,4,6-trimethyl-[1,3,5,2,4,6]trioxatrisilinane, 2,4,6-tris-[2-(dimethoxy-methyl-silanyl)-ethyl]-2,4,6-trimethyl-[1,3,5,2,4,6]trioxatrisilinane, 2,4,6-tris-[2-(triethoxy-silanyl)-ethyl]-2,4,6-trimethyl-[1,3,5,2,4,6]trioxatrisilinane, and mixtures thereof.

16. A moisture-curable sealant, coating or adhesive made from the moisture-curable composition of claim 11.

17. A cured moisture-curable resin composition made by curing the moisture-curable resin composition of claim 11.

\* \* \* \* \*